US005481476A

United States Patent [19]
Windig

[11] Patent Number: 5,481,476
[45] Date of Patent: Jan. 2, 1996

[54] APPARATUS FOR INTERACTIVE SELF-MODELING MIXTURE ANALYSIS

[75] Inventor: Willem Windig, Rochester, N.Y.

[73] Assignee: Eastman Kodak Company, Rochester, N.Y.

[21] Appl. No.: 379,829

[22] Filed: Jan. 27, 1995

Related U.S. Application Data

[63] Continuation of Ser. No. 532,601, Jun. 4, 1990, abandoned.

[51] Int. Cl.$^6$ ................................................ G06F 159/00
[52] U.S. Cl. ............................ 364/498; 364/500; 73/23.2
[58] Field of Search ..................................... 364/497, 498, 364/499, 500, 554; 73/23.2, 23.22, 23.1; 250/339

[56] References Cited

U.S. PATENT DOCUMENTS

| | | | |
|---|---|---|---|
| 4,343,242 | 10/1982 | Harris et al. ............................. | 73/23.1 |
| 4,800,279 | 1/1989 | Hieftje et al. ........................... | 250/339 |
| 4,807,148 | 2/1989 | Lacey ....................................... | 364/498 |
| 4,837,726 | 6/1989 | Hunkapiller ............................. | 364/498 |
| 4,941,101 | 7/1990 | Crilly ....................................... | 364/497 |

OTHER PUBLICATIONS

J. C. Hamilton et al, "Mixture Analysis Using Factor Analysis II; Self–Modeling Curve Resolution," *J. Chemometrics*, 4, 1990, pp. 1–13.
Willem Windig et al, "Fast Self–Modeling Curve–Resolution Method for Time–Resolved Mass Spectral Data," *Anal. Chem.*, 1988, 60, pp. 1503–1510.
Keiji Sasaki et al, "Estimation of Component Spectral Curves from Unknown Mixture Spectra," *Applied Optics*, 15 Jun. 1984, vol. 23, No. 12, pp. 1955–59.
Windig et al, "Nonsupervised Numerical Component Extraction from Pyrolysis Mass Spectra of Complex Mixtures," *Anal. Chem.* 1984, 56, pp. 2297–2303.
Friedrich et al, "Combinations of Orthogonal Spectra to Estimate Component Spectra in Multicomponent Mixtures," *Applied Spectroscopy*, vol. 41, No. 2, 1987, pp. 227–234.
Liu et al, "Data Processing Techniques to Extract Pure–Component Spectra from Mixture Spectra and Their Application to Polymeric Systems," 1987, *Anal. Chem.* 1987, 59, pp. 2609–2615.
Lacey, "Deconvolution of Overlapping Chromatographic Peaks," *Anal. Chem.*, 1986, 58, pp. 1404–1410.

*Primary Examiner*—Vincent N. Trans
*Attorney, Agent, or Firm*—Charles E. Snee, III

[57] ABSTRACT

An apparatus for analyzing spectral data of a mixture having a plurality of components by determining the pure variables, each of which has a contribution from only one of the mixture components, includes a programmed computer for performing steps of a) providing spectral data of the mixture, b) determining purity values of variables from said data to provide a first purity spectrum, c) finding the maximum of the purity values to determine the first pure variable, d) calculating a determinant-based weight function with respect to said first pure variable, e) multiplying the first purity spectrum by the determinant-based weight function to provide a second purity spectrum, f) finding the maximum in the second purity spectrum to yield the second pure variable, g) repeating steps d),e) and f) for successive determinant-based weight functions with respect to preceding pure variables to provide successive purity spectra from which successive pure variables are found. The pure variables so determined are compared and the results of the comparison used control a process in which the mixture undergoes a reaction.

18 Claims, 32 Drawing Sheets

FIG. 4A  1st PURITY SPECTRUM RITTERI
FIG. 4B  1st STANDARD DEVIATION SPECTRUM RITTERI
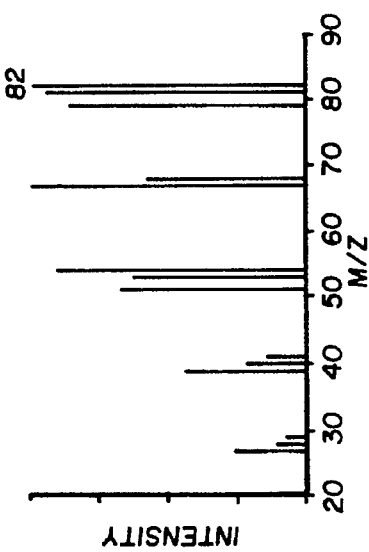
FIG. 4C  DETERMINANT SPECTRUM RITTERI

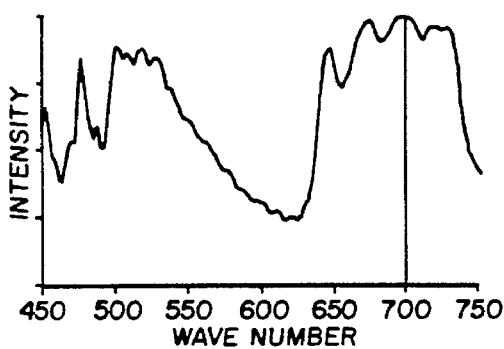
FIG. 7A — 1st PURITY SPECTRUM TMOS
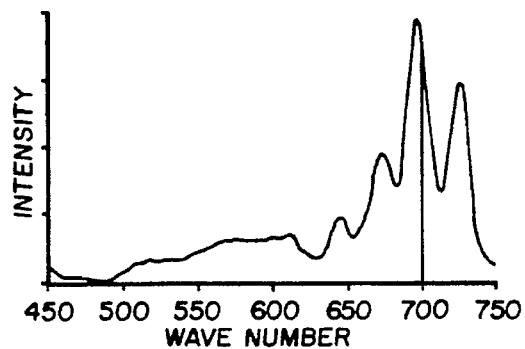
FIG. 7B — 1st STANDARD DEVIATION SPECTRUM TMOS
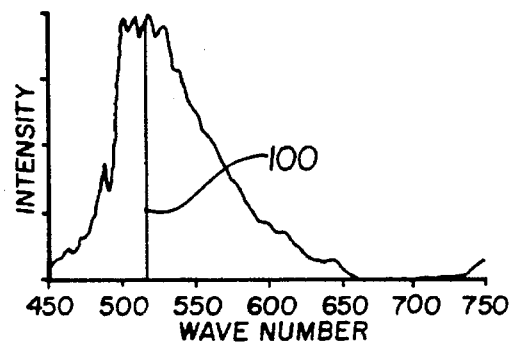
FIG. 7C — 2nd PURITY SPECTRUM TMOS
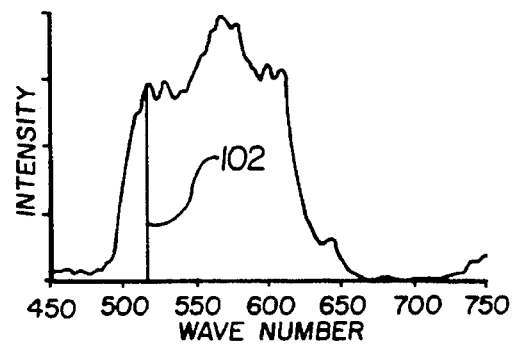
FIG. 7D — 2nd STANDARD DEVIATION SPECTRUM TMOS
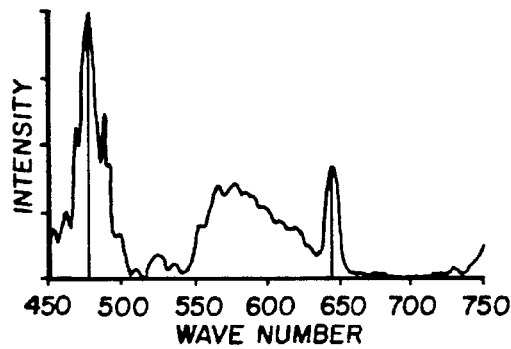
FIG. 7E — 3rd PURITY SPECTRUM TMOS
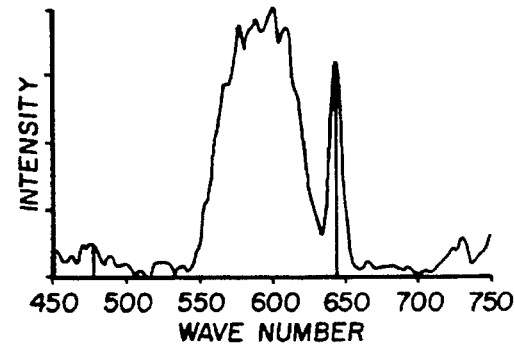
FIG. 7F — 3rd STANDARD DEVIATION SPECTRUM TMOS 4th PURITY SPECTRUM TMOS 4th STANDARD DEVIATION SPECTRUM TMOS 5th PURITY SPECTRUM TMOS 5th STANDARD DEVIATION SPECTRUM TMOS

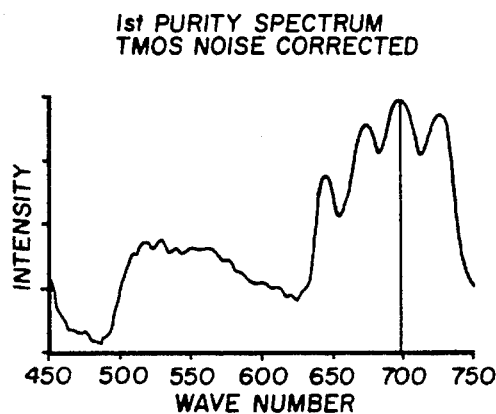
FIG. 9A — 1st PURITY SPECTRUM TMOS NOISE CORRECTED
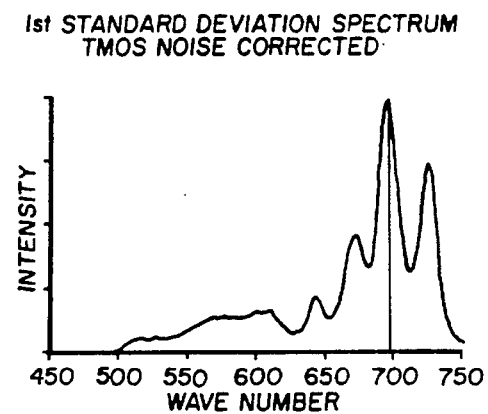
FIG. 9B — 1st STANDARD DEVIATION SPECTRUM TMOS NOISE CORRECTED
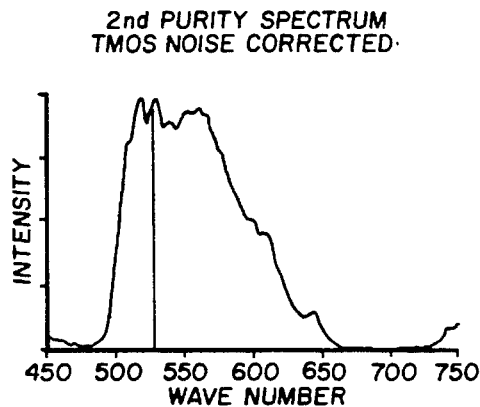
FIG. 9C — 2nd PURITY SPECTRUM TMOS NOISE CORRECTED
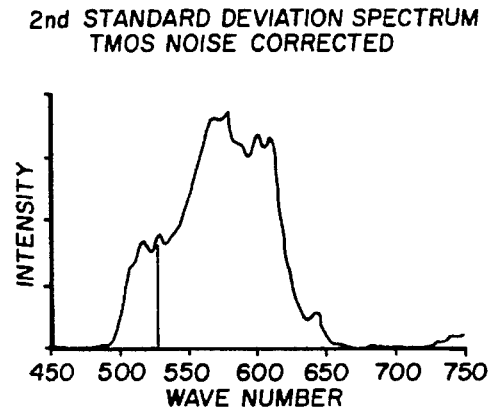
FIG. 9D — 2nd STANDARD DEVIATION SPECTRUM TMOS NOISE CORRECTED
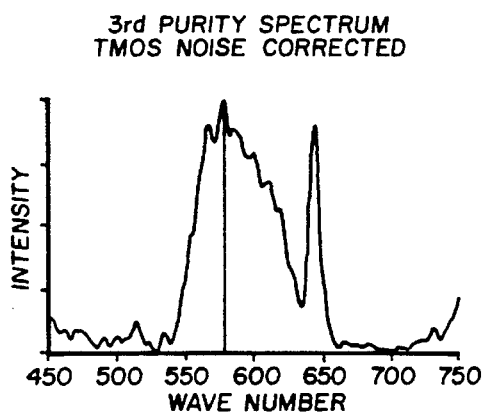
FIG. 9E — 3rd PURITY SPECTRUM TMOS NOISE CORRECTED
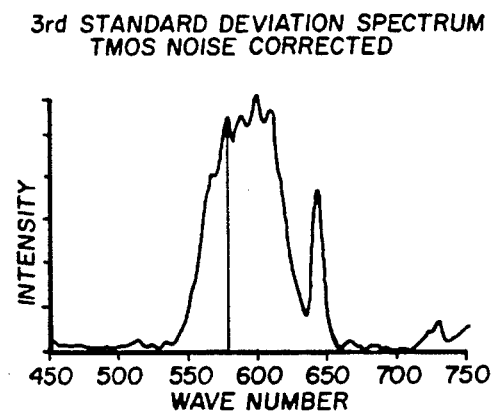
FIG. 9F — 3rd STANDARD DEVIATION SPECTRUM TMOS NOISE CORRECTED

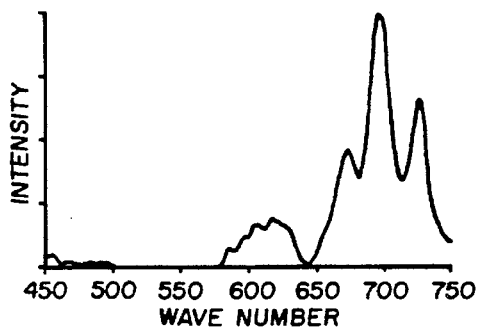
FIG. 10A — 1st RESOLVED COMPONENT TMOS
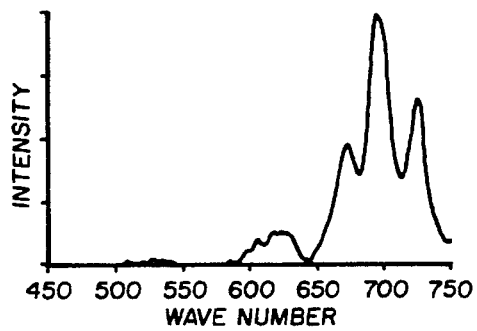
FIG. 10B — RESOLVED COMPONENT PCA TMOS
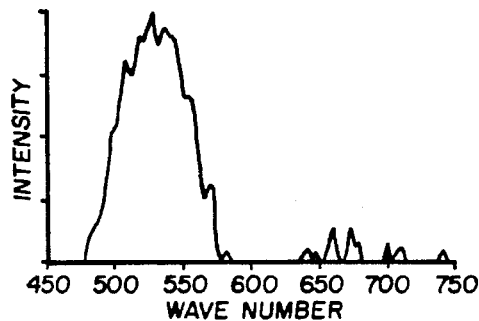
FIG. 10C — 2nd RESOLVED COMPONENT TMOS
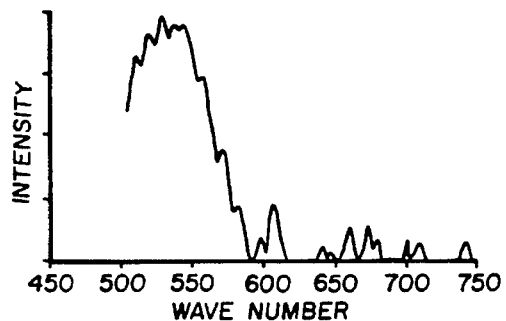
FIG. 10D — RESOLVED COMPONENT PCA TMOS
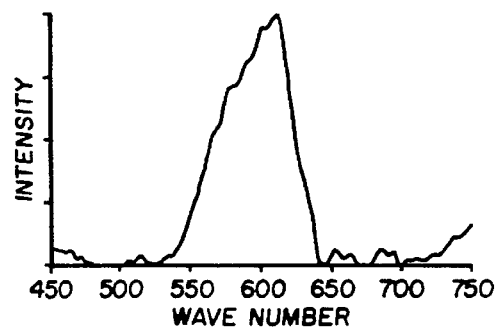
FIG. 10E — 3rd RESOLVED COMPONENT TMOS
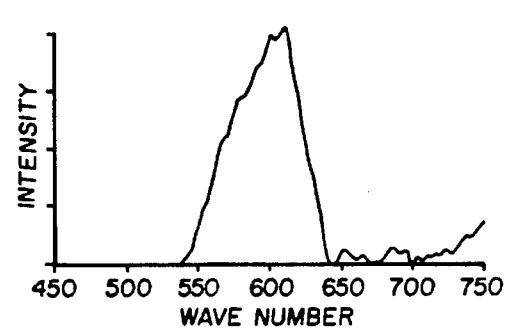
FIG. 10F — RESOLVED COMPONENT PCA TMOS

APPARATUS FOR INTERACTIVE SELF-MODELING MIXTURE ANALYSIS

CROSS REFERENCE TO RELATED APPLICATION

This application is a continuation of Ser. No. 07/532,601, filed 4 Jun. 1990, now abandoned.

BACKGROUND OF THE INVENTION

This invention relates to the art of quantitative and qualitative mixture analysis, and more particularly to a new and improved apparatus for resolving spectral data of mixtures in terms of pure components and concentrations without the use of reference data in the form of known spectra or known concentrations.

In the analytical environment, despite the use of hyphenated and/or high resolution analytical instruments, the resulting spectral data often represents mixtures of several components. Furthermore, reference spectra are not always available to resolve the mixture data by techniques such as least squares or spectral subtraction. Accordingly, to extract information about pure components often is a major problem. For this type of problem, self-modeling mixture analysis techniques have been developed. Generally, the term curve resolution is used for the approaches of the type provided by the present invention. But since this technique is not limited to "curve" types of data, such as resulting from hyphenated instruments, the term self-modeling mixture analysis is used. Most prior art self-modeling techniques are based on principal component analysis. Principal component analysis is well suited for this type of problem because of the noise reduction that can be obtained by the use of the proper number of principal components and because of the ability to find pure variables, i.e. variables that have an intensity for only one of the components of the mixtures under consideration.

Although principal component analysis is presently the state-of-the-art approach for self-modeling curve resolution, it is far from a routine laboratory method. A notable exception is a commercially available apparatus which employs diode-array chromatographic detectors. This approach, however, is limited to resolving two components. There are several reasons for the limited success of principal component analysis as a routine tool. One is that despite the considerable amount of work done in the area of error analysis, there is no established method to determine the proper number of principal components to use. A second reason is that there is great reluctance to use principal component analysis, mainly due to the fact that principal component analysis does not lend itself easily to the development of user friendly programs that can be run with the same ease as, for example, library search programs for mass spectral matching. Thus, these techniques require highly skilled operators, due to the complexity of the algorithms used, and no general purpose software is available.

It would, therefore, be highly desirable to provide a new and improved apparatus for resolving spectral data of mixtures which is simple to use and does not require the use of reference data in the form of known spectra or known concentrations. It would be advantageous to provide such an apparatus which facilitates user interaction and which makes self-modeling mixture analysis more accessible for general use.

SUMMARY OF THE INVENTION

The present invention provides an apparatus for resolving spectral or other data of mixtures in terms of pure components and concentrations without the use of reference data in the form of known spectra or known concentrations. The apparatus is based on a pure variable-based method, pure variables being those variables which have contributions from only one of the components in the mixture. The pure variables are determined without the use of principal component analysis but by simpler means. In accordance with the invention, all the intermediate steps can be presented in the form of spectra, which highly facilitates user interaction, and it is possible to direct the search procedure for the pure variables.

The apparatus of the present invention determines the purity as the ratio of the standard deviation and the mean of the intensities of the variable. The resulting purity values can be plotted in the form of a spectrum, which highly facilitates user interactions. In addition to this so-called first purity spectrum, the standard deviation values can be used for a first standard deviation spectrum, in order to facilitate the evaluation of the purity spectrum in comparison with the original data. The variable with the maximum intensity in the first purity spectrum determines the first pure variable.

In order to eliminate the effect of the first pure variable, a determinant-based weight function is calculated. This function has a value of zero for the first pure variable and high values for the other pure variables. The second purity spectrum (and standard deviation spectrum) are obtained by multiplying the first purity spectrum (and standard deviation spectrum) by the determinant-based weight function.

The next pure variable is again the one with the maximum intensity in the purity spectrum. The next purity spectrum can be calculated again by a determinant-based weight function, which then gives the value zero for the first and second pure variables, and all linear combinations thereof. This process is continued until the purity and standard deviation spectra do not show spectral features anymore, i.e. they only show a noise pattern. The total intensity of the purity spectrum, the total intensity of the standard deviation spectrum and the sum of the elements of the determinant-based weight function can also be used in order to determine how many components are present in the mixture, since these intensities should approach zero after determining all the pure variables.

Since intensities in the noise range may behave like pure variables, a correction is applied by adding a small value to the denominator part (the mean) of the purity calculation. A typical value is 5% of the maximum value of the mean. Other values can be used, for example a function based on the mean of the mean values of the variables. Similarly, the determinant calculations are corrected for low intensities.

The pure variables are used, in combination with the original data set, to obtain the spectra of the pure components. This is done by a standard least squares technique. Finally, the concentrations of the components are calculated by using the extracted pure component spectra in combinations with the original data set by a least squares method again. The intensities of the (scaled) pure variables can also be used for the concentrations, but the extra least squares step acts as a noise reduction step.

As a result, the apparatus of the present invention expresses all its intermediate results in terms of spectra, which highly facilitates user interaction. In the event there are cases where pure variables are unacceptable, e.g. for reasons of noise or since they describe unwanted effects such as interactions, the operator can optimize and direct the process. The purity value is calculated in a new way and is a function of the standard deviation, the mean and the determinant function, in combination with the two error correction terms discussed above. Especially since these purity values can be displayed in the form the operator is most familiar with (i.e., the spectrum), this is easier to understand intuitively than the complex mathematics of eigenvector based algorithms, used until now. Not only the extracted components, but also the concentrations are calculated by least squares methods, which result in a noise reduction. The apparatus is particularly useful for resolving spectral mixture data in a type of batch mode. The apparatus is advantageously employed in process monitoring and control.

The foregoing and additional advantages and characterizing features of the present invention will become clearly apparent upon a reading of the ensuing detailed description together with the included drawing wherein:

BRIEF DESCRIPTION OF THE DRAWING FIGURES

FIGS. 4a–4e are graphics including spectral representations of the pure variable search according to the method of the present invention;

FIGS. 7a–7j are graphs including purity and standard deviation spectra resulting from the pure variable search according to the method of the present invention wherein the pure variables are indicated by vertical lines within the spectra;

FIG. 9a–9j are graphs including purity and standard deviation spectra similar to those of FIG. 7 after being corrected for noise;

FIGS. 10a–10h are graphs including purity spectra wherein FIGS. 10a,c,e and g are based on pure variables extracted by the method of the present invention and FIGS. 10b, d,f and ha are based on pure variables extracted by principal component analysis;

FIGS. 24g is a combination of the spectra of FIGS. 24a and e;

DETAILED DESCRIPTION OF THE ILLUSTRATED EMBODIMENTS

The mode of operation of the present invention will be explained in two ways, the first by using a mixture data set presented in the following Table I.

TABLE I

| Mixture No. Concentrations | Composition Of Mixtures In Relative Concentrations | | |
|---|---|---|---|
| | Relative Component | | |
| | A | B | C |
| 1 | 0.34 | 0.34 | 0.32 |
| 2 | 0.44 | 0.23 | 0.33 |
| 3 | 0.48 | 0.25 | 0.27 |
| 4 | 0.20 | 0.35 | 0.45 |
| 5 | 0.21 | 0.51 | 0.28 |
| 6 | 0.22 | 0.54 | 0.24 |
| 7 | 0.44 | 0.37 | 0.19 |
| 8 | 0.17 | 0.54 | 0.29 |
| 9 | 0.33 | 0.05 | 0.62 |

TABLE I-continued

Composition Of Mixtures In
Relative Concentrations

| Mixture No. Concentrations | Relative Component | | |
|---|---|---|---|
| | A | B | C |
| 10 | 0.19 | 0.37 | 0.44 |
| 11 | 1.00 | 0.00 | 0.00 |
| 12 | 0.00 | 1.00 | 0.00 |
| 13 | 0.00 | 0.00 | 1.00 |

Figure 1:
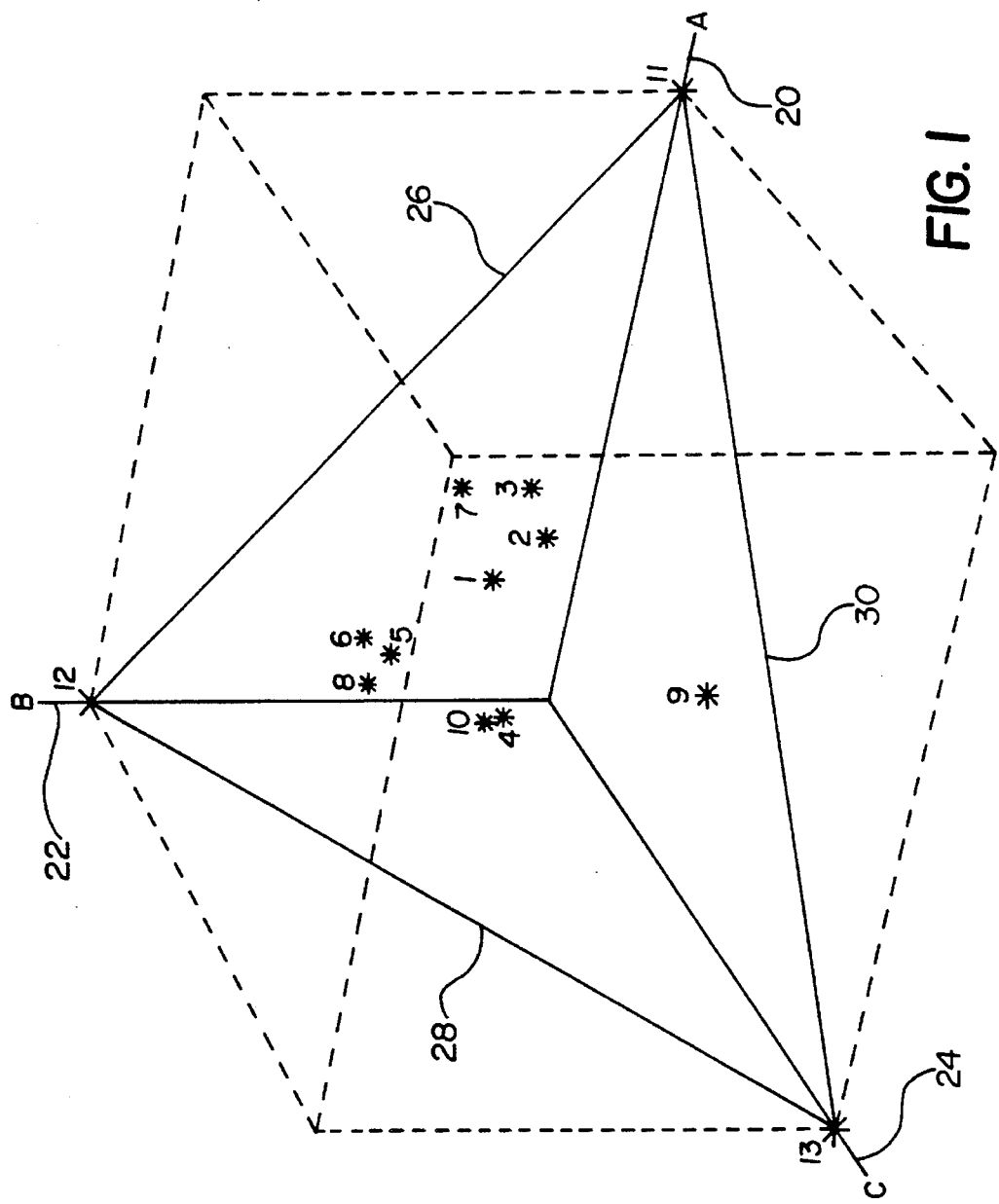
FIG. 1 is a plot of the data set of Table I in a three dimensional axes system.

A plot of this data set in a three dimensional axes system is given in FIG. 1 wherein the A, B and C component axes are designated 20, 22 and 24, respectively. The data points lie in a plane, because the sum of the three concentrations is constant, i.e. one. This causes the loss of one degree of freedom. In other words, the system contains three independent variables, but since the sum of the three variables is known to be one, once the values of two of the variables are known, the value of the third is automatically known. That is the one degree of freedom which is lost. The plane in which the mixtures lie is limited by a triangle formed by the three pure components, the sides of the triangle being designated 26, 28 and 30 in FIG. 1. Each of the data points is obtained by first locating the values of the A, B and C components on the respective axes 20, 22 and 24 and then on each axis projecting a perpendicular line. The intersection of the three lines defines a data point and the thirteen data points from the mixture data set of Table I are located in the triangular plane bounded by the sides 26, 28 and 30 in FIG. 1. For example, consider mixture no. 1 in Table I. The A,B, and C component concentration 0.34, 0.34 and 0.32 are located on the A, B and C axes, respectively, designated also 20, 22 and 24 in FIG. 1. The three perpendicular lines from those points on the A, B and C axes intersect at data point 1 in FIG. 1. Considering data point 2, it has a slightly higher A component concentration, slightly lower B concentration and substantially similar C concentration as compared to data point 1. This corresponds to the relative position of point 2 in FIG. 1 as compared to point 1 wherein point 2 is further along the A axis and closer to the origin along the B axis. By way of further explanation, data point 11 has maximum (1.00) A concentration and zero B and C concentrations and thus it is located on the A axis at 1.0 and being on the A axis has zero B and C values.

Figure 2:
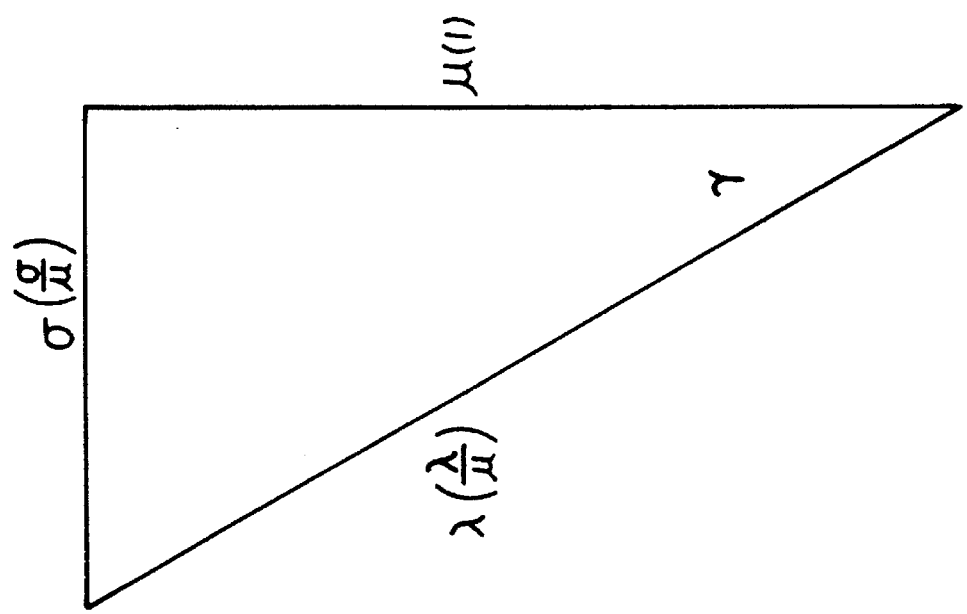
FIG. 2 is a drawing representing a projection onto the triangular plane of FIG. 1 of a vectorial representation of a variable having a length limited by the triangular plane of FIG. 1.

In practice, a mixture data set will consist of hundreds of variables, e.g. m/z (mass/charge #) values for mass spectrometry and wavenumbers of FTIR (Fourier Transform Infra- Red). Assuming a spectral mixture data set with the same composition as given in Table 1, the variables will have contributions from one or more of the components. As a result, every variable will be a positive linear combination of the three component axes. As a consequence, each variable will be bracketed by, i.e. located within, the three component axes 20, 22, 24 as presented in FIG. 1. If each of these variables is represented by a vector of which the length is limited by the triangular plane, the projection of these variables onto the triangle will result in FIG. 2, similar to the known triangular three component mixture plots. In FIG. 2, λ is the magnitude of the variable, μ is the mean determined from all spectra and is the standard deviation which lies in the aforementioned triangular plane. The position of a vector in this triangle of FIG. 2 gives a direct measure of the contributions of the three components A, B and C. All the variables will project within a triangle spanned by the three component axes 20, 22 and 24. A variable that has only contributions from one of the components, a so called pure variable, will coincide with the corresponding component axis. If one does not know the pure variables of a data set and there are reasons to assume the presence of pure variables, it will be clear that the first pure variable can be found by determining the vector with the largest length in the triangular plot. From this plot it is also clear where the other two variables are present. It must be stressed, that the presence of pure components in the data set is not required to obtain this type of results according to the method of the present invention; the only requirement is the presence of pure variables.

Triangular plots like the foregoing can be obtained by known principal component analysis and form the bases of a visually aided self-modeling curve resolution method, the known variance diagram technique. This latter technique can be used in combination with the mathematically oriented pure variable approach to resolve mixtures. In accordance with the present invention, it has been determined that since the lengths of the variable vectors in this triangle are determined by their purity, it is possible to plot a spectrum that represents the purity, using the lengths of these vectors for the intensity axis: a variable with a relatively high intensity will be relatively pure, a variable with a low intensity will have contributions from several components. Furthermore, as mentioned above, the variable with the highest intensity is the first pure variable. The presentation of purity values in the form of a spectrum, in accordance with the present invention, is more directly related to the original data and lends itself better for a user friendly approach than the loading type of plots such as shown in FIG. 2 and forms the basis for the present invention. Although the plot shown in FIG. 2 is based on principal component analysis, the lengths (purity) of the variable vectors in the triangle can be calculated without the use of principal component analysis, as will now be explained.

The data matrix is represented by D, size v* c, where v is the number of variables (rows), and c the number of cases or spectra (columns). The length $\lambda_i$ of a variable i is:

$$\lambda_i = \sqrt{\left(\left(1/c \sum_{j=1}^{c} d_{i,j}\right)^2\right)} \qquad \text{(equation 1)}$$

wherein d is each data value in the matrix in row i, column j.

The relation between the length, the mean and the standard deviation is as follows where λ i is the length of variable i:

$$\lambda_i^2 = \mu_i + \sigma_i^2 \qquad \text{(equation 2);}$$

where μ i is the mean of variable i:

$$\mu_i = (1/c) \sum_{j=1}^{c} d_{i,j}; \qquad \text{(equation 3)}$$

and $\sigma_i$ is the standard deviation of variable i:

$$\sigma_i \sqrt{\left(\left(1/c \sum_{j=1}^{c} (d_{i,j} - \mu_i)^2\right)\right)} \qquad \text{(equation 4)}$$

Figure 3:
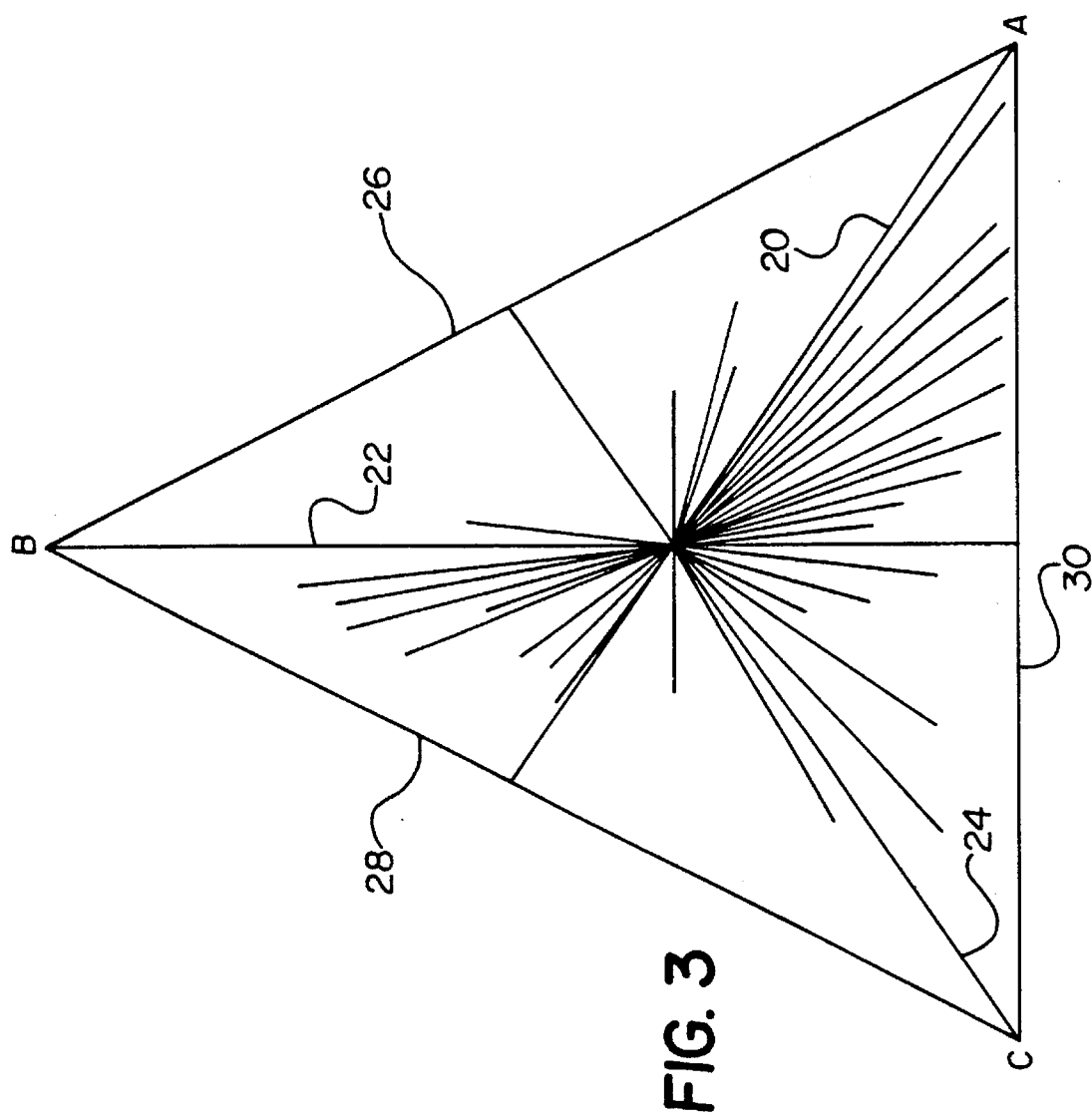
FIG. 3 is a graph of the vector representations of the mathematical relationship between the length, mean and standard deviation of a variable in a data set.

The vector representation of the relation described by equation 2 is given in FIG. 3. Realizing that the mean of the data set lies in the triangle, see FIG. 1, it is possible to rationalize the relation between FIG. 1 and FIG. 3. The vector labeled μ represents the perpendicular distance between the origin of that particular variable and the triangular plane; the vector labeled λ represents the vector of that variable with length λ. The vector labeled G now represents the contribution of that variable in the mixture triangle. The value of o does not represent the purity as presented in FIG. 2, though, since every variable vector will have a different length. Furthermore, every variable has a different mean and standard deviation because of the different spectra. A proper way to scale the variable vectors is in such a way, that their vectors are limited by the triangular plane as given in FIG. 1. In other words, it is desired that every variable have the same mean. Accordingly the vector length, mean and standard deviation represented in FIG. 2 each is divided by the mean to limit the vectors within the triangle. The quantities within parentheses in FIG. 2 are the values after dividing by the mean. Variables scaled in this fashion will project within the triangle, as in FIG. 2. As a consequence, the purity of variable i as graphically represented in FIG. 3 is defined by:

$$P_{i,1} = \sigma_i / \mu_i \qquad \text{(equation 5)}$$

The second subscript of the purity value p indicates that this is the first purity value. As will be shown, other purity values will be calculated. The purity value represents tan γ, where γ represents the angle between the vectors $\mu_i$ and $\lambda_i$. The length of each of the lines within the triangle of FIG. 3 is $\sigma_i / \mu_i = \tan \gamma$.

At this point, the relation between the purity value as defined in equation 5 and purity values referred to in the prior art need to be established. The factor analysis method and the key-set method define the first pure variable as the one with the lowest projection in the first principal component, after scaling the loadings by their lengths. This is equivalent to cos γ in FIG. 3. There is also a relation with a prior art method of three component curve resolution in order to determine the purity of a spectrum. In that method, the purest ("simplest") spectrum is defined as the one with the smallest area norm ratio in the principal component space. Calculating the mean and length of rows instead of columns of the matrix results in the area and the norm. As a consequence, the area norm ratio is the $(\cos \gamma)^{-1}$. Although the cos and tan are approximately the same for small angles, it will be clear from the knowledge of these geometrical functions that the tan will give more distinct purity values.

The elimination of the effect of the mean vector is also the basis of the calculation of FIG. 2. In order to obtain this triangle, the data matrix D transformed to the matrix D(g) in the following way:

$$d(\mu)_{i,j} = (d_{i,j} - \mu_1) / \mu_1 \qquad \text{(equation 6)}$$

The significance of equation 6 is as follows. In order to locate the variables on the same surface, i.e. the plane of the triangle previously described, the mean must be subtracted from the data values. In order to bracket or locate all the variables within the boundary of the surface, i.e. within the sides of the aforementioned-mentioned triangle, it is necessary to divide the above result by the mean. The length of the transformed variables equals $p_{i,1}$, as can be easily derived by applying equation 1 on the transformed elements $d(\mu)_{i,j}$. Principal component analysis on the simulated data set described above results in two principal components, of which the loading plot shown in FIG. 3 is the basis of the triangular plot in FIG. 2.

Although the mode of operation of the present invention is rationalized above by using a normalized mixture system, it is not necessary to have a normalized system. The principle behind the whole system is that the more independent sources of variance there are, the smaller the standard deviation becomes with respect to the mean: the principle of signal averaging. This is due to the fact that the combined mean of the independent sources is the simple sum of the mean values, while the combined variance is the sum of squares of the variance values of the independent sources.

To summarize the foregoing, it is possible to calculate the length of the projection of variable vectors onto a common surface, i.e. the triangular plane as graphically represented in FIG. 2, by applying equation 5 wherein the purity of the variable is the ratio of the standard deviation to the mean.

Due to the scaling by the mean, the purity spectrum is not directly comparable with the original spectra in a data set. Especially when variables with a low intensity in the original spectra have a high purity, a visual comparison may be hard. In order to facilitate the comparison of the purity spectrum with the original data, the multiplication of the purity spectrum with the mean values, resulting in the standard deviation spectrum, is appropriate. This latter spectrum has intensities related with the intensity changes in the original data. The relation of the standard deviation spectrum with the purity spectrum as well as the original data makes the standard deviation spectrum a suitable visual aid in the pure variable search.

In order to further describe and illustrate the present invention, data sets from prior art literature will be utilized. In particular such data sets are obtained from G. L. Ritter, S. R. Lowry, T. L. Isenhour and C. L. Wilkins in "Factor Analysis of the Mass Spectra of Mixture", *Analytical Chemistry*, 48, 1976 p. 591–595. These data sets are evaluated by F. J. Knorr and J. H. Futrell in "Separation Of Mass Spectra Of Mixtures by Factor Analysis", *Analytical Chemistry*, 51, 1979 p 1236–1241 and by E. R. Malinowski in "Obtaining The Key Set Of Typical Vectors by Factor Analysis and Subsequent Isolation of Component Spectra", *Analytical Chemistry*, 134, 1982 p. 129–137. The first data set from Ritter, referred to herein as Ritter 1 data set, consists of the mass spectra of 4 cyclohexane/cyclohexene mixtures, reported to contain 0.79, 0.58, 0.38 and 0.19 mol fraction cyclohexane. Another mass spectral data set described by Ritter contained a cyclohexane/hexane mixture, reported to contain 1.00, 0.92, 0.83, 0.55, 0.23, 0.12 and 0.00 mol fraction cyclohexane, respectively. A leak in the mass spectrometer introduced nitrogen as a third component. The data set was analyzed including the contribution of nitrogen (m/z 28) which will be referred to as Ritter 2a, and without the contribution of m/z 28, which will be referred to as Ritter 2b.

In the following description, the term "variables" will be used for the entities in which the spectra are measured, such as wavenumbers. The term "cases" is used for spectra, and in a broader sense spectra can be considered to be responses.

Figure 4E:
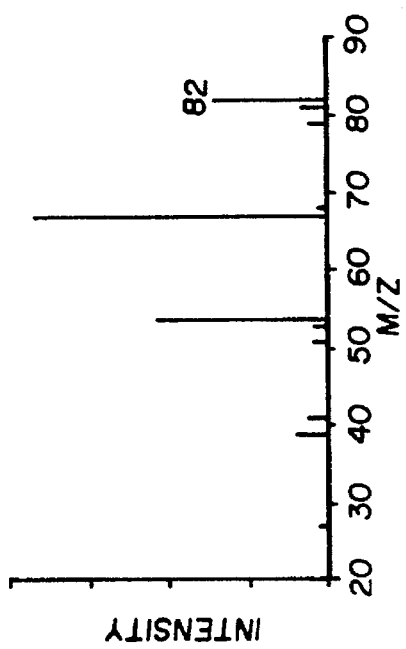

Applying equation 5 to the Ritter 1 data set results in the values plotted in FIG. 4a which is a graph of intensity or magnitude of purity as a function of m/z values. The variable with the highest purity appears to be m/z 84 which is the same one as found by Knorr and Futrell and Malinowski. As discussed above, the purity values as given in FIG. 4a are based on mean scaled variables. Although this is indeed necessary to determine the purity, it is also convenient to multiply the purity of the variables by their mean values, which facilitates comparison with the original data. Equation 5, shows that this will result in the standard deviation spectrum. The spectrum representing the purity values $p_{i,1}$ will be called the first purity spectrum. The spectrum resulting from multiplying $pi_1$ by $\mu_i$ will be called the first standard deviation spectrum, and is presented in FIG. 4b. As will be shown, both representations need to be used in combination for a proper evaluation of the data set.

The next step in the mode of operation of the present invention is to determine the next, i.e. second, pure variable. The purity spectrum and the standard deviation spectrum are based on all the components. Because the pure variables are variables that bracket, i.e. limit or confine within, all the other variables in the configuration illustrated by FIG. 1, the next pure variable is the one that is most independent of the first pure variable. It is also important to determine the rank of the data matrix, since the rank is determined by the number of components in the data set. The independence of variables and the rank of a matrix can be determined by a determinant-based function according to the present invention.

The determinant-based function employed in the present invention is called a determinant spectrum, of which the elements are calculated as follows. First, the correlation around the origin (COO) matrix needs to be calculated. The COO dispersion matrix has been chosen since it gives all the variables an equal contribution in the calculations. If this is not done, the determinant is not only proportional to the independence of the variables, but also to the length of the variables. In order to calculate the COO matrix, the data matrix first needs to be scaled by the length:

$$d(\lambda)_{i,j} = d_{i,j}/\lambda_i \quad \text{(equation 7)}$$

The COO matrix now equals:

$$C = (1/c)D(\lambda)^T D(\lambda)^T \quad \text{(equation 8)}$$

By way of further illustration, consider two variables represented by vectors having lengths 1A and 1B which extend from a common point or original and which define therebetween an acute angle θ. The larger the angle θ, the more independent are the variables 1A and 1B and vice versa. Consider next a parallelogram wherein vectors 1A and 1B are two adjacent sides thereof meeting at the angle θ. The determinant calculates the area of the parallelogram for this two v dimensional case. In order to make the determinant a function only of the angle θ, which is a measure of the degree to which the variables are related or nonrelated, the variables must be divided by the lengths.

The next step is to calculate the following determinants:

$$W_{i,2} = \begin{Vmatrix} C_{i,i} & C_{i,p} \\ C_{p,i} & C_{p,p} \end{Vmatrix} \quad \text{(equation 9)}$$

where p is the index of the first pure variable. Since the matrix C is symmetric and has ones on its diagonal because of the COO matrix, eq. equation 9 can be simplified to:

$$W_{i,2} = \begin{Vmatrix} 1 & C_{i,p} \\ C_{i,p} & 1 \end{Vmatrix} \quad \text{(equation 10)}$$

The use of a value 2 for the second subscript rather than one will be explained subsequently. The values of $W_{i,2}$ will be proportional to the same measure as to which the variables i and p are independent. This can be rationalized by knowing that the determinant calculates the surface area of a parallelogram defined by the row (or column) vectors of the elements of C given in equations 9 and 10. If variables are highly correlated, the angle between the vector representation of these variables will be small, which will result in a small determinant (surface of parallelogram) defined by these vectors, with a minimum value of 0. Variables that do not have any relation with each other have a maximum value of 1, since the diagonal elements of the matrix in equations 9 and 10 equal 1 (due to the length scaling of the COO matrix). As a consequence, variables highly correlated with the pure variable have a value for $w_{i,1}$ close to 0, while variables which are dissimilar to the pure variable have a high value.

In the prior art, a determinant based function is applied to principal component analysis results. Although the combination of the purity values and the determinant based weight function give better results than just the determinant based function, the use of only the determinant based function is an option in the software utilizing the invention. It should be noted that the determinant in the prior art method is based on principal component analysis in contrast to the invention.

The result of the foregoing calculation is presented in FIG. 4c. This spectrum can in principle be used to determine the next pure variable. The variable with the highest intensity in the determinant spectrum is m/z 82, which is the same variable as found by Knorr and Futrell and Malinowski. The determinant does not express the purity, however. For example, a variable that is shared by the three components as illustrated in FIG. 1 will have an intermediate value in the determinant calculation, while it will have a 0 value in the purity calculations. Therefore, the determinant spectrum is used as a weight function for the purity spectrum. As a consequence, the elements of the purity spectrum now become:

$$P_{i,2} = (\sigma_i/\mu_i) * W_{i,2} \quad \text{(equation 11)}$$

Figure 4D:
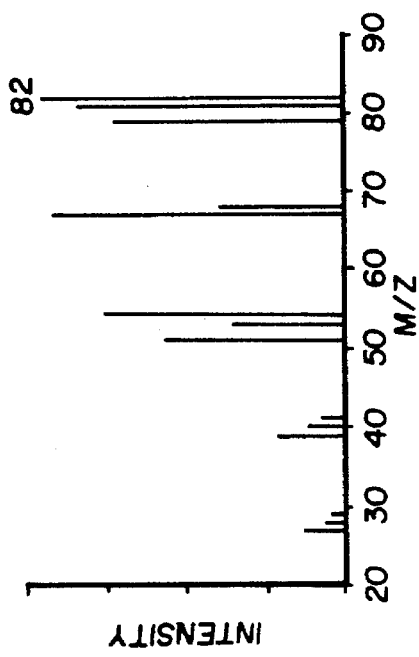

The resulting spectrum is called the second purity spectrum and is given in FIG. 4d. Although there are not many differences between the determinant spectrum in FIG. 4c and the second purity spectrum in FIG. 4d, it is more obvious in the latter representation that m/z 82 is the purest variable. Also, variables that are shared by the two components, i.e. m/z 27–29, have a clearly lower intensity in the second purity spectrum than in the determinant spectrum. Altogether, there are more pronounced differences within the second purity spectrum than in the determinant spectra, which facilitates the process of pure variable selection. The second purity values multiplied by their respective mean values results in FIG. 4e. This spectrum is called the second standard deviation spectrum.

By way of further example, FIG. 5 illustrates the foregoing procedure for inspecting the variables to determine their relation to the pure variables. In FIGS. 5a–5d the rectangle designated 60 represents schematically the product of the length-scaled matrix D and its transpose as set forth in equations 7 and 8. In particular, the product of the v x c matrix with the c x v matrix results in the v x v matrix 60. This is the COO matrix previously described. In FIG. 5a, Va represents the first pure variable and $V_i$ represents the first variable to compare. The four intersections 61, 62, 63 and 64 are the values for the first determinant to be calculated. The closer the value of the determinant calculation is to one, the greater is the difference in value between variable $V_1$ and pure variable $V_A$. FIG. 5b illustrates a similar procedure for comparing the next variable $V_2$ to the pure variable $V_A$. The four intersections 65, 66, 67 and 68 are the values for the determinant to be calculated. In a similar manner, depending upon whether the calculated value of the determinant is close to zero or 1, the variable $V_2$ is close to or remote from the pure variable $V_A$.

Figure 5A:
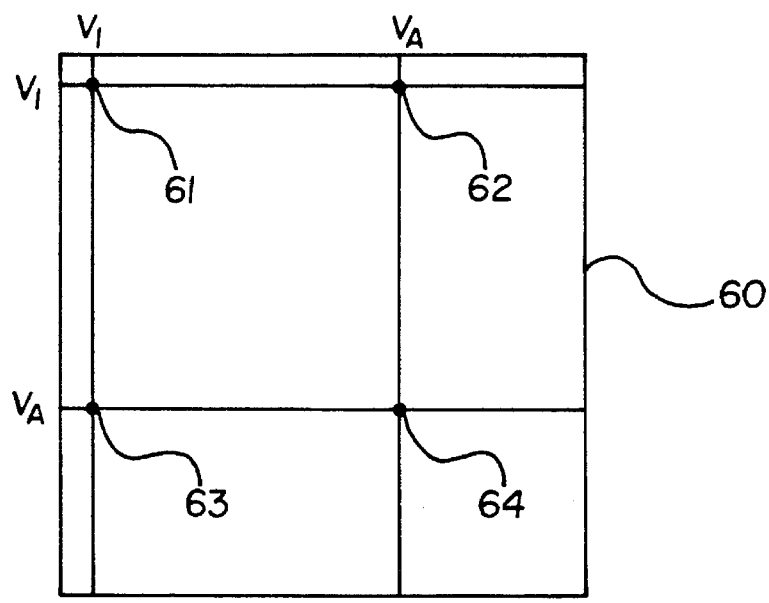
FIGS. 5a–5d are schematic diagrams illustrating the determinant-based method according to the present invention for comparing variables to pure variables.
Figure 5B:
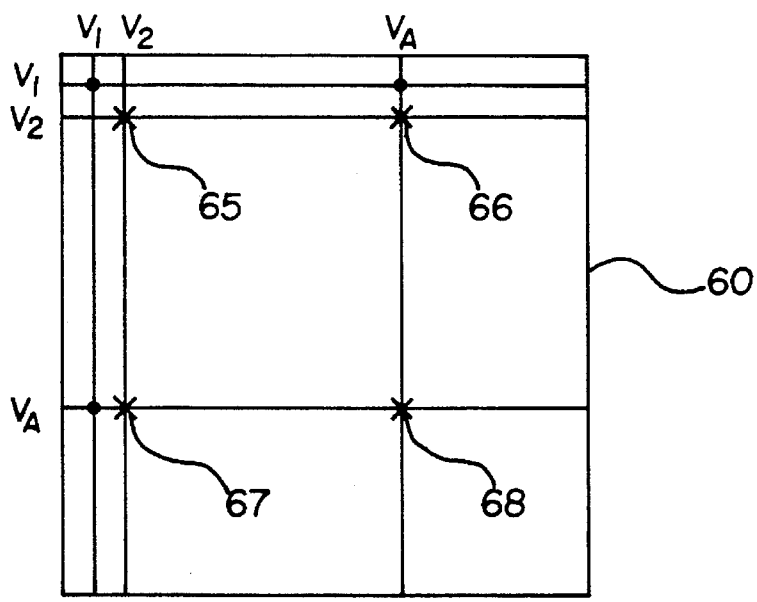
Figure 5C:
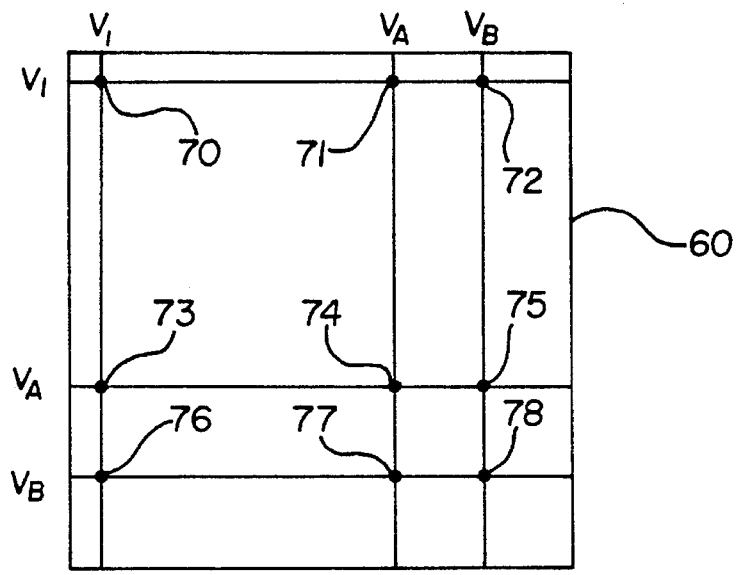
Figure 5D:
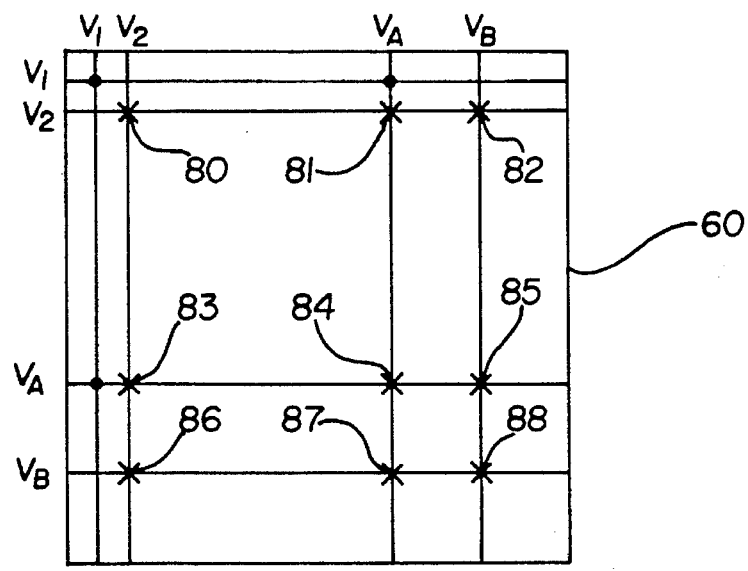

FIG. 5c illustrates the foregoing procedure with the first two pure variables $V_A$ and $V_B$ wherein the variable $V_1$ is compared. The nine intersections 70, 71, 72, 73, 74, 75, 76, 77 and 78 are the values for the determinant to be calculated. Thus, when a variable is compared to two pure variables, a 3×3 determinant is calculated, as compared to the 2×2 determinant when a variable is compared to one pure variable. FIG. 5d illustrates the procedure in comparing the variable $V_2$ to the two pure variables. The nine intersections 80, 81, 82, 83, 84, 85, 86, 87, and 88 are the values for the determinant to be calculated.

The next step is to determine whether the pure variables selected so far account for all the components or if there is more information left. If the two pure variables are, indeed representative of the whole mixture system, all other variables in the data set will be linear combinations of the two pure variables, which will result in zero values for the determinant function introduced in equation 9, but now extended to account for the effect of both the first and second pure variable:

$$W_{i,3} = \begin{Vmatrix} C_{i,i} & C_{i,p} & C_{i,q} \\ C_{p,i} & C_{p,p} & C_{p,q} \\ C_{q,i} & C_{q,p} & C_{q,q} \end{Vmatrix} \quad \text{(equation 12)}$$

In a manner similar to that of equation 11, the third purity spectrum is calculated as follows:

$$P_{i,3} = (\sigma_i/\mu_i) * W_{i,3} \quad \text{(equation 13)}$$

or, in a general formulation:

$$P_{i,j} = (\sigma_i/\mu_i) * W_{i,j} \quad \text{(equation 14)}$$

Where j represents the number of pure variables selected plus one. At this point $w_{i,1}$ needs to be defined. The maximum value for the determinants equals 1, due to the use of variables scaled to unit length. As a consequence, the values for the determinant based weight function are one before any pure variables have been accounted for.

$$W_{i,1} = 1 \quad \text{(equation 15)}$$

For the data set under discussion, all the $w_{i,3}$ values should be zero (due to noise the values will only approach 0) if the pure variables with the index p and q represent all the components in the mixtures. A possible candidate for determining the rank of the system after determining j pure variables is based on the averaged value of the determinants:

$$R_{dj} = 100 * (1/v) \sum_{i=1}^{\checkmark} w_{i,j} / \sum_{i=1}^{\checkmark} w_{i,1} w_{i,1} \quad \text{(equation 16)}$$

This function will have a maximum value of 100, which then is the value before any pure variables have been determined. As a consequence, the values can be considered as relative values with respect to the determinant prior to extracting pure variables. Another function based on the total intensity of the purity values relative to the value of the total intensity of the first purity spectrum after determining j pure variables is:

$$R_{pj} = 100 * \sum_{i=1}^{\checkmark} P_{i,j} / \sum_{i=1}^{\checkmark} P_{i,1} \quad \text{(equation 17)}$$

Yet another function is based on the intensity of the standard deviation spectra, relative to the total intensity of the first standard deviation spectrum:

$$R_{js} = 100 * \sum_{i=1}^{\checkmark} (p_{i,j} * \mu_i) / \left( \sum_{i=1}^{\checkmark} P_{i,1} * \mu_i \right) \quad \text{(equation 18)}$$

The advantage of the latter function is that it includes the intensity of the variables through the contributions of variables in the noise range. In practice, it appears that equation 18 gives the best results for determining the rank of the data set. The ratio of the successive values for this function facilitates this process.

$$Rr_j = R_{sj}/R_{s(j+1)} \quad \text{(equation 19)}$$

Since the value of Rsj becomes close to 0 after using the proper number of pure variables, the value for this function will be relatively high after determining the proper number of pure variables.

Other stop-criteria may be based on the sum of the squares of the purity spectrum, standard deviation spectrum or the determinant based weight function. Functions based on ratios of these sums, similar to Functions based on ratios of these sums, similar to prior art principal component analysis based on criteria, are also suitable.

From Table II it is clear that 11 the information in the data set has been accounted for by the two pure variables selected: the third value (i.e. the value after eliminating the effect of the first two variable) for Rd, $^R p$ and $^R s$ is negligible with respect to the previous ones, and, as a consequence, the second value for $R_r$ is high. In Table II, A represents cyclohexane and B represents cyclohexene.

TABLE II

Results of the mode of operation of the invention compared with results of Knorr and Futrell and Ritter 1 data set Values of functions to determine rank.

| $R_d$ | $R_p$ | $R_s$ | $R_r$ |
|---|---|---|---|
| 100.0000 | 100.0000 | 100.0000 | 5.9413 |
| 16.2486 | 16.6556 | 16.8314 | 273.5315 |
| 0.1070 | 0.0957 | 0.0615 | |

Concentrations

| Knorr and Futrell | | Invention | | Molar fractions | | |
|---|---|---|---|---|---|---|
| | | | | | Knorr and | |
| A | B | A | B | Ritter | Futrell | Invention |
| 54.1 | 14.2 | 54.7 | 14.4 | .79 | .79 | .79 |
| 56.0 | 35.6 | 56.7 | 36.2 | .58 | .61 | .61 |
| 42.8 | 52.2 | 43.4 | 53.1 | .38 | .45 | .45 |
| 12.4 | 48.6 | 12.5 | 49.4 | .19 | .20 | .20 |

Resolved component spectra

| | Knorr and Futrell | | Invention | |
|---|---|---|---|---|
| Mass | A | B | A | B |
| 27 | 13 | 11 | 13 | 12 |
| 28 | 7 | 3 | 7 | 3 |
| 29 | 7 | 2 | 7 | 2 |

TABLE II-continued

Results of the mode of operation of the invention
compared with
results of Knorr and Futrell and Ritter 1 data set
Values of functions to determine rank.

| 39 | 18  | 28  | 19  | 29  |
|----|-----|-----|-----|-----|
| 40 | 4   | 3   | 4   | 3   |
| 41 | 52  | 29  | 52  | 29  |
| 42 | 24  | 2   | 24  | 2   |
| 43 | 11  | 0   | 11  | 1   |
| 51 | 2   | 7   | 2   | 7   |
| 53 | 3   | 9   | 4   | 10  |
| 54 | 5   | 66  | 5   | 66  |
| 55 | 34  | 5   | 34  | 5   |
| 56 | 100 | 2   | 100 | 2   |
| 67 | 0   | 100 | 0   | 100 |
| 68 | 2   | 5   | 2   | 5   |
| 69 | 29  | 0   | 29  | 0   |
| 79 | 0   | 6   | 1   | 7   |
| 81 | 0   | 9   | 0   | 9   |
| 82 | 0   | 37  | 0   | 37  |
| 84 | 78  | 0   | 79  | 0   |

Now that the pure variables have been determined, the data set can be resolved into the pure components and their contributions in the original spectra. The data matrix D can be expressed as a mixture system by the following equation:

$$D^T = C P \quad \text{(equation 20)}$$

where $D^T$ (size c*v) contains mixture spectra in its rows. The matrix C (size c*n), where n is the number of pure components, contains the relative amount of the pure components in the mixture spectra in its columns, and the matrix P (size n*v) contains the (unknown) spectra of the pure components in its rows. For the pure variable approach, the intensities of the pure variables in the spectra in D are used in C. As a consequence, $D^T$ and C are known, and P can be resolved by a least squares method:

$$P = (C^T C)^{-1} C^T D^T \quad \text{(equation 21)}$$

Assuming that every component results in the same response in the instrument, concentrations can be calculated based on spectra in matrix P that are normalized. This normalization procedure is described by the following equations:

$$f_1 = \sum_{j=1}^{v} P_{i,j} \quad \text{(equation 22)}$$

The inverse values of f1 are used for diagonal elements of the matrix N, which then can be used to normalize the spectra in P.

$$Q = NP \quad \text{(equation 23)}$$

where Q (size n*v) contain the normalized spectra. Although the intensities of the pure variables (after correcting for the normalization procedure described above) can be used for the concentrations, it was decided to obtain the concentrations by a least squares method, since this results in a noise elimination similar to principal component analysis. Applying the same least squares approach as described in equation 20, the least squares approximation for the concentrations is:

$$A = (D^T D)^{-1} D^T Q^T \quad \text{(equation 24)}$$

A (size c*n) now contains the concentrations of the pure components in the mixture spectra. The concentrations, molar fractions, and spectra obtained by the present invention are given in Table II. Comparison with the values obtained by Knorr and Futrell show a high degree of similarity, which shows the feasibility of the mode of operation of the present invention.

The Ritter 2a and Ritter 2b data sets, described hereinabove, are the next subject for the evaluation of the present invention. The values for the relative intensities of the determinant, purity and standard deviation spectra for the Ritter 2a data set (including m/z 28) are given in Table III, which supports the conclusion that three components are available. The extracted spectra and concentrations are again almost identical to the results of Knorr and Futrell (not shown). The complete results obtained from the data set after deleting m/z 28, i.e., the Ritter 2b data, are also given in Table III. Comparison with the results of Knorr and Futrell again show almost perfect agreement. In Table II, A represents cyclohexane and B represents cyclohexene.

TABLE III

Results of the mode of operation of the invention
compared with
results of Knorr and Futrell and Ritter 2 data set
Values of functions to determine rank.

| $R_d$ | $R_p$ | $R_s$ | $R_r$ |
|---|---|---|---|
| \multicolumn{4}{c}{Ritter 2a (m/z 28 included)} |
| 100.0000 | 1000.0000 | 100.0000 | 2.7567 |
| 40.9214 | 42.8494 | 36.2750 | 24.7342 |
| 1.4780 | 1.7655 | 1.4666 | 60.1166 |
| 0.0857 | 0.0679 | 0.0244 | |
| \multicolumn{4}{c}{Ritter 2b (m/z 28 excluded)} |
| 100.000 | 100.0000 | 100.0000 | 2.7617 |
| 41.1479 | 43.3414 | 36.2100 | 200.1774 |
| 0.5539 | 0.5425 | 0.1809 | |

Concentrations

| Knorr and Futrell | | Invention | | Molar fractions | | |
|---|---|---|---|---|---|---|
| | | | | | Knorr and | |
| A | B | A | B | Ritter | Futrell | Invention |
| 53.1 | 2.3 | 53.4 | 2.2 | 1.00 | 0.96 | 0.96 |
| 41.9 | 7.7 | 42.3 | 7.4 | 0.92 | 0.84 | 0.85 |
| 44.3 | 12.2 | 44.8 | 12.3 | 0.83 | 0.78 | 0.78 |
| 35.5 | 30.3 | 35.8 | 30.8 | 0.55 | 0.54 | 0.54 |
| 18.7 | 43.0 | 18.8 | 42.6 | 0.23 | 0.30 | 0.31 |
| 9.9 | 48.4 | 9.8 | 48.1 | 0.12 | 0.17 | 0.17 |
| 0.8 | 55.3 | 0.6 | 54.8 | 0.00 | 0.01 | 0.01 |

Resolved component spectra

| | Knorr and Futrell | | Invention | |
|---|---|---|---|---|
| Mass | A | B | A | B |
| 27 | 13 | 23 | 13 | 23 |
| 29 | 8 | 40 | 8 | 40 |
| 39 | 17 | 13 | 17 | 13 |
| 40 | 5 | 2 | 5 | 2 |
| 41 | 51 | 71 | 51 | 71 |
| 42 | 24 | 37 | 25 | 37 |
| 43 | 13 | 71 | 14 | 71 |
| 44 | 1 | 2 | 1 | 2 |
| 54 | 6 | 5 | 6 | 1 |
| 55 | 35 | 6 | 35 | 6 |
| 56 | 100 | 55 | 100 | 55 |
| 57 | 5 | 100 | 5 | 100 |
| 69 | 30 | 2 | 30 | 2 |
| 83 | 5 | 1 | 5 | 1 |
| 84 | 79 | 0 | 79 | 0 |
| 85 | 7 | 1 | 7 | 1 |
| 86 | 0 | 23 | 0 | 24 |

Another data set for illustrating the mode of operation of the present invention, which will be referred to as the TMOS data set, results from a study of the formation of silica glasses from solutions of tetra-alkoxysilanes by the sol-gel process, which provides a promising route to low temperature glass films and monoliths. The study was reported by J. L. Lippert, S. B. Melpolder and L. M. Kelts in "Raman Spectroscopic Determination of the pH Dependence of intermediates on Sol-Gel Silicate Formation", *Journal Non-Crystalline Solids*, 104, 1988, p. 139–147. In order to get a better understanding of the process, the time dependence of the sol-gel hydrolysis and condensation of $Si(OCH_3)_4$ (tetramethyl orthosilicate, abbreviated TMOS) in aqueous methanol is studied. The starting material TMOS has a reported Raman shift at 644 $cm^{-1}$, respectively. The products of this reaction are:

a) Hydrolysis products: $Si(OCH_3)_n(OH)_{4-n}$. The Raman shifts for n=3, 2, 1 are 673, 696, 726 $cm^{-1}$, respectively.

b) Condensation products: $Si(OSi)m(OR^*)_3.OR^*$ is $CH_3$ or H. The Raman shifts for m=1, 2 are 608 (shoulder at 586) and 525 $cm^1$, respectively. These products will be indicated as the first and second condensation product.

Figure 6:
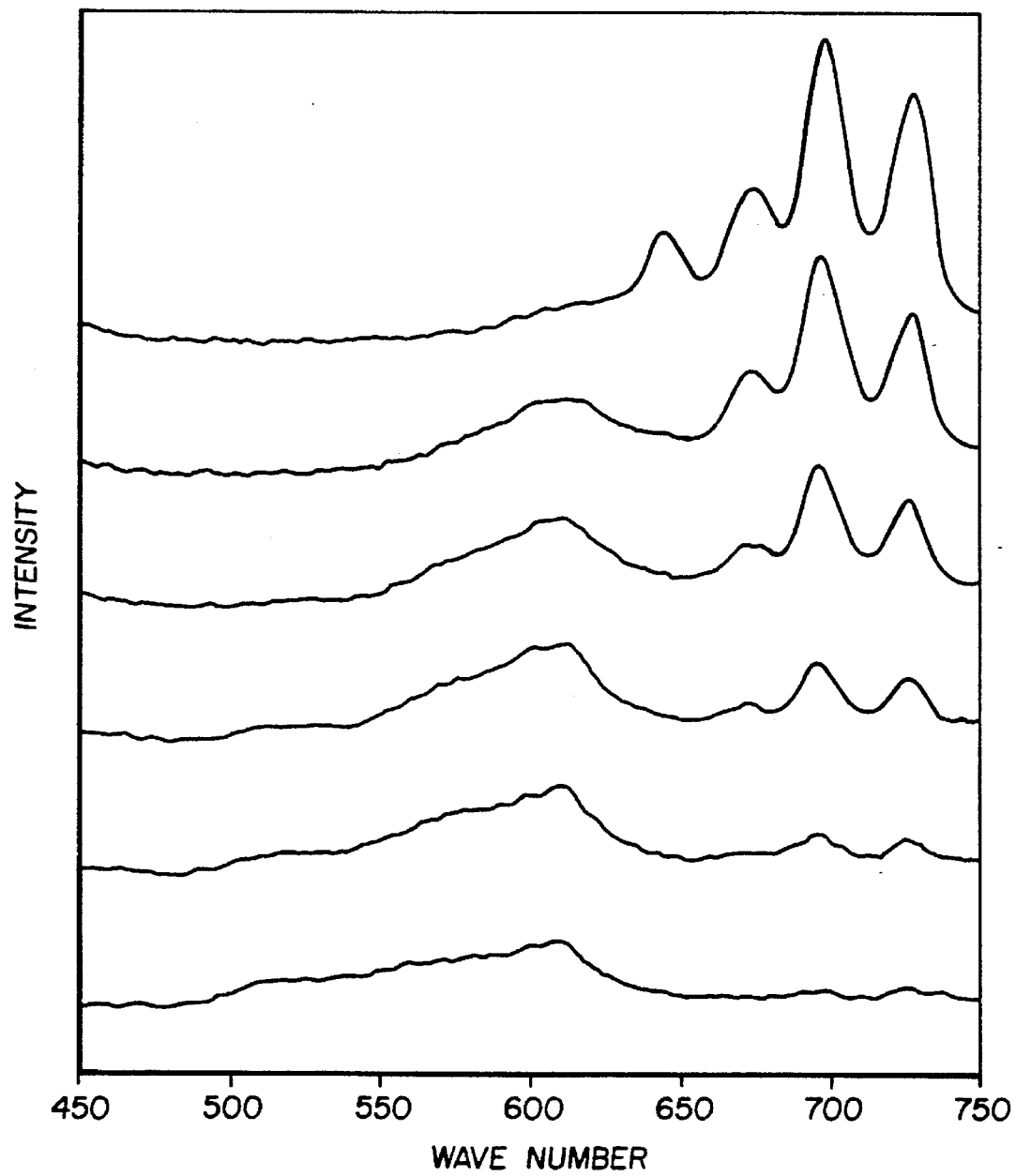
FIG. 6 is a graph of spectra from another data set wherein the time sequence proceeds from top to bottom in the figure.
Figure 7G:
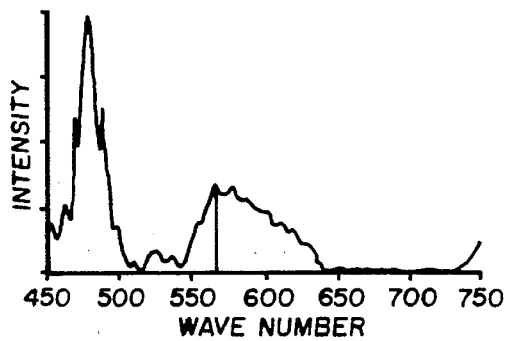
Figure 7H:
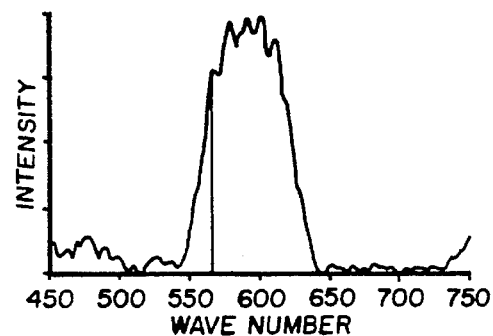
Figure 7I:
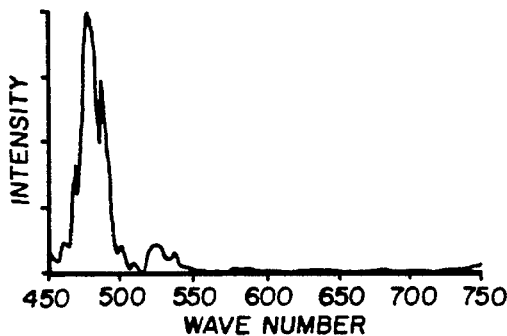
Figure 7J:
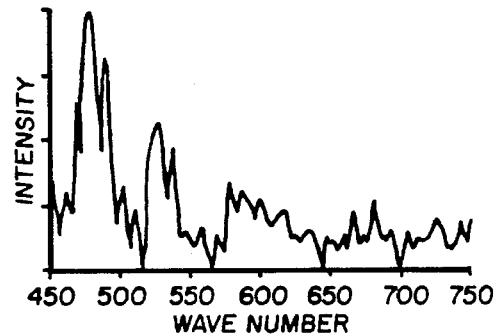
Figure 8:
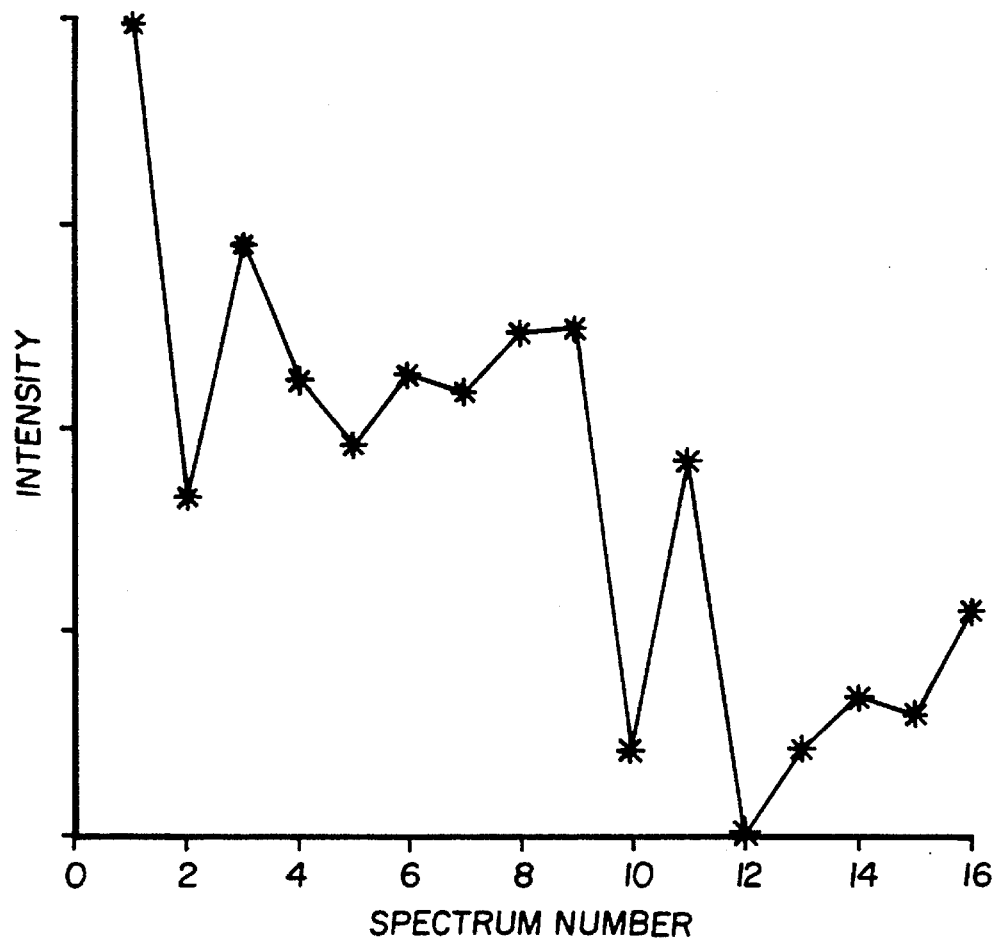
FIG. 8 is a graph including a plot of the intensities of a particular wavenumber in time.
Figure 9G:
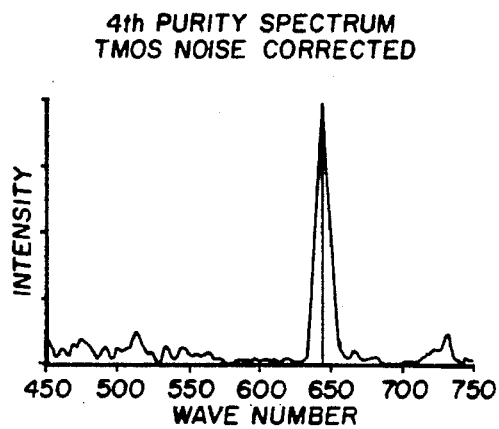
Figure 9H:
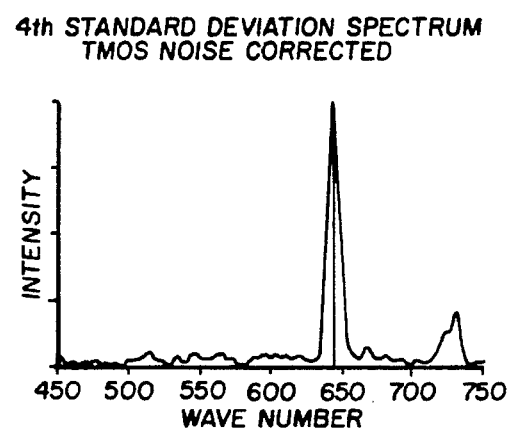
Figure 9I:
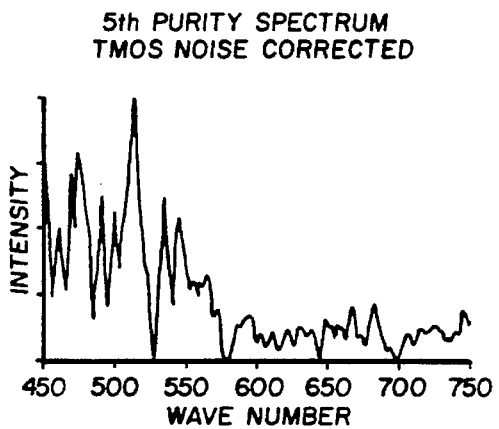
Figure 9J:
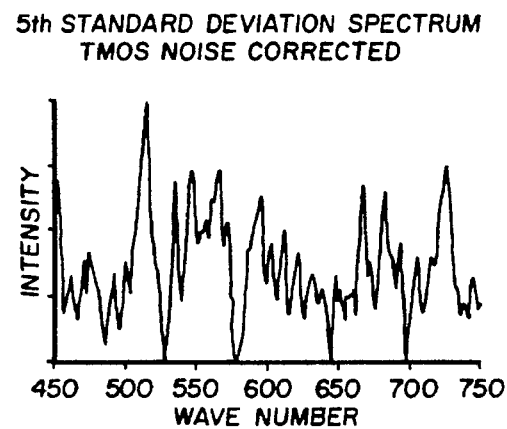

A sample of the spectra of the TMOS data set is given in FIG. 6. The first purity and standard deviation spectra are given in FIG. 7a,b. The maximum intensity is at 700 $cm^{-1}$, which therefore is the first pure variable. The intensities of the wavenumber form a smooth curve (not shown), as can be expected from a time resolved data set, and is accepted as the first pure variable. After eliminating the effect of the first pure variable by using equations 7–11, the second purity and second standard deviation spectra are the ones designated 100 and 102 in FIG. 7c,d. This results in the selection of the next pure variable, i.e. 516 $cm^{-1}$, which is accepted as the next pure variable. The third purity and standard deviation spectra are given in FIG. 7e, f. The maximum in the purity spectrum in FIG. 7e is at 478 $cm^{-1}$. The peak that displays this maximum, has an odd shape, however. Furthermore, the standard deviation spectrum shows that this wavenumber is in a low intensity area, which may indicate that this pure variable is caused by noise. A plot of the intensities at 478 $cm^{-1}$ versus time in FIG. 8 shows an erratic behavior, while a more or less continuous curve is expected from a time resolved reaction. In combination with the low intensity it is a strong indication that this is a noise peak. The peak around wavenumber 478 is now inactivated for the pure variable search, which can be done interactively with a cursor in the program of the present invention which will be described. The next pure variable then is 644 $cm^{-1}$. The fourth purity and standard deviation spectra are given in FIG. 7g,h. Ignoring the lower wavenumber range again, the pure variable selected is 566 $cm^{-1}$. After elimination of the effect of this pure variable, the fifth purity spectrum and standard deviation spectrum clearly consist of only noise, which shows that the process is complete. This is also confirmed by the diagnostic values presented in Table IV.

TABLE IV

| Results From the Invention With TMOS Data Values of functions to determine rank | | | |
|---|---|---|---|
| $R_d$ | $R_p$ | $R_s$ | $R_r$ |
| 5.9444 | 100.0000 | 100.0000 | 100.0000 |
| 9.7213 | 34.5462 | 30.9193 | 16.8225 |
|  | 3.3932 | 2.4671 | 1.7305 |

TABLE IV-continued

| Results From the Invention With TMOS Data Values of functions to determine rank | | | |
|---|---|---|---|
| $R_d$ | $R_p$ | $R_s$ | $R_r$ |
| 24.0025 |  |  |  |
|  | 0.1580 | 0.1124 | 0.0721 |
| 113.5285 |  |  |  |
|  | 0.0038 | 0.0035 | 0.0006 |
|  |  | Noise Corrected |  |
|  | 100.0000 | 100.0000 | 100.0000 |
| 9.1018 |  |  |  |
|  | 16.6101 | 16.0453 | 10.9868 |
| 16.8073 |  |  |  |
|  | 0.8380 | 0.7013 | 0.6737 |
| 72.2108 |  |  |  |
|  | 0.0113 | 0.0134 | 0.0091 |
| 97.7223 |  |  |  |
|  | 0.0000 | 0.0002 | 0.0001 |

It is now possible to resolve the TMOS data set, using the pure variable information. Before this is done, a closer look is taken at the noise problem which interfered with the pure variable search described above. The purity value was high in the region around 478 $cm^{-1}$, while it was relatively low in the standard deviation spectrum of FIG. 7e,f. Since the difference between the purity spectrum and the standard deviation spectrum is a multiplication by the mean, it is obvious that the noisy area has relatively low values for the mean. Since the purity value is the ratio of the standard deviation and the mean, it is clear that the high purity value was due to a relatively low mean value. A simple procedure is possible to correct for this. A small value is added to the mean values which results in the following noise corrected version of equation 5.:

$$P_{i,j}=\sigma_i/(\mu_1+o) \qquad \text{(equation 25)}$$

If $\sigma$ has a relatively low value with respect to $\mu_i$ the effect will be negligible, but for low values of $\mu_1$ (in the noise range) the effect is that the purity will make the purity value low, which is exactly what is needed in order to correct for noise. Next to this low intensity correction for the purity value, the same procedure can be applied to the calculations of the determinant, in order to give variables with a low length a lower weight in the calculations. Equation 7 then changes into:

$$d(\lambda_1\beta)_{i,j}=d_{i,j}/(\lambda_i+\beta) \qquad \text{(equation 26)}$$

The COO matrix is then calculated as given in equation 8, using these corrected values. The resulting determinants are referred to by $w(\beta)_{i,j}$. As was discussed above, before any pure variables are extracted, the determinant values for each of the variables are 1, which is the maximum value for the determinants. With the correction described in equation 25, the maximum lengths are different. In order to be consistent, the values for the weightfactor for the first purity spectrum need to be calculated as follows:

$$w(\beta)_{i,j}=[\lambda_i/(\lambda_i+\beta)]^2 \qquad \text{(equation 27)}$$

The associated standard deviation spectrum is obtained again by simply multiplying the values by the mean. It appears that a value for $\alpha$ of 5% of the maximum value of $\mu_1$ and a value of 5% of the maximum value of $\lambda_i$ results in purity and standard deviation spectra with the noise virtually eliminated, as shown in FIG. 9. The pure variables selected now do not include wavenumbers with intensities in the noise range. The pure variables selected in FIG. 8 are very close to the ones selected in FIG. 7, although the pure variables for the noise corrected data resulted in a higher similarity with the results obtained by principal component analysis based mixture resolution. The values give by equations 16–19, given in Table 4 appear to be of limited value: it is not clear whether three or four pure variables are present. It is, however, very clear from the fifth purity and standard deviation spectra presented in FIGS. 9 *i,h*, that there are only four pure variables. The problem with the diagnostic values is probably caused by the fact that TMOS, the last component to be resolved in FIG. 9, has such a low contribution in the data set, as can be judged from the original spectra in FIG. 6. Furthermore, as every spectroscopist knows, a complex pattern such as a spectrum can not be captured adequately in one single number, which limits the values of functions to determine the rank of a matrix.

Figures 10G, 10H:
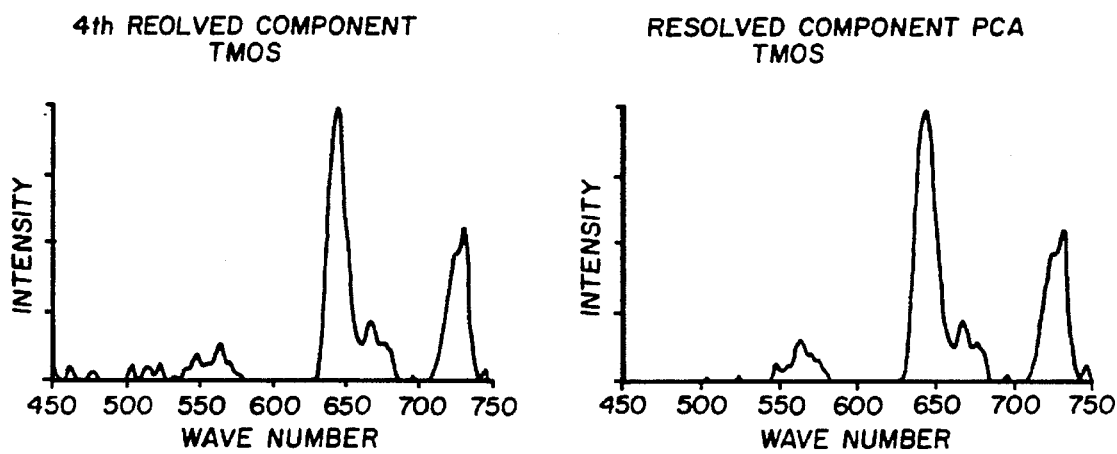
Figure 11B:
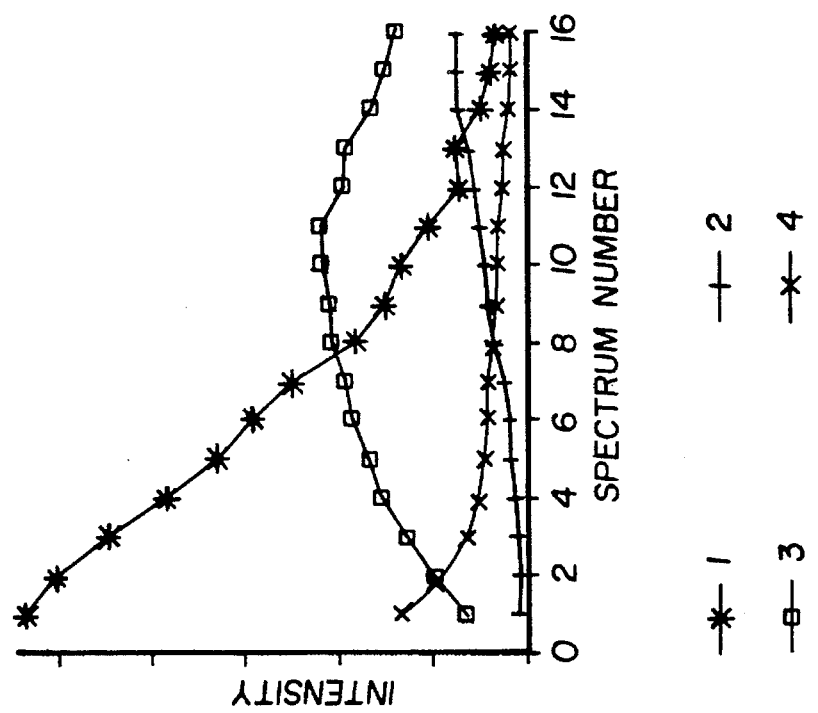
FIGS. 11a and 11b are graphs including concentration profiles extracted by the method of the present invention and by principal component analysis respectively.
Figure 11A:
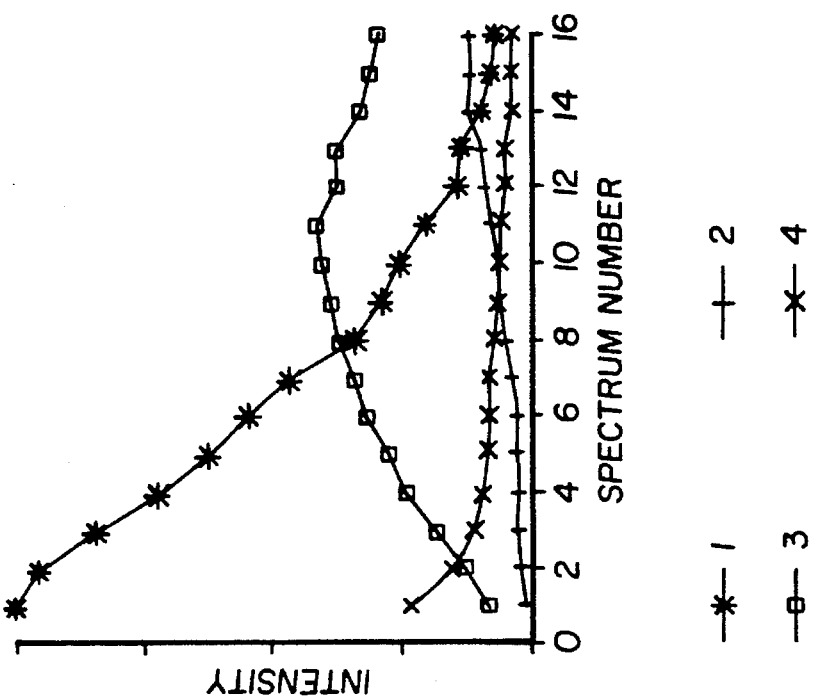

For resolving the mixtures, the pure variables selected as described in FIG. 9 are used. The spectra and concentration profiles resulting from these pure variables are given in FIGS. 10 and 11, respectively. In order to compare the results obtained before by using the principal component analysis, these results are also given in FIG. 10 and 11. The results are almost identical. The first extracted spectrum is associated with the hydrolysis products. Due to a high correlation between the three hydrolysis products, it was not possible to separate them. The pure wavenumber selected by the method of the invention was 698, which is close to the one reported in literature, i.e. 696. The spectrum in FIG. 10*b* clearly related to the second condensation product, and was calculated on the basis of 528 cm$^{-1}$ as the pure variable, with a reported value of 525 cm–1, which is again very close. The spectrum presented in FIG. 10*e* represents the first condensation product and is based on 578 cm$^{-1}$ as a pure variable, with a reported pure variable of 608 cm$^{-1}$ and 586 cm$^{-1}$. This is a broad peak, which is very likely the cause for the relatively large differences between the value determined by the invention and the literature value. The most striking feature, however, is the agreement with the results obtained by principal component analysis, see FIGS. 10 *bdfh*, respectively. Finally, the spectrum in FIG. 10*d* represents the starting material TMOS, with a pure variable at 644 cm$^{-1}$, which corresponds exactly with the literature value. The concentration profiles are given in FIG. 11 in agreement with expectations and known features.

Figure 12:
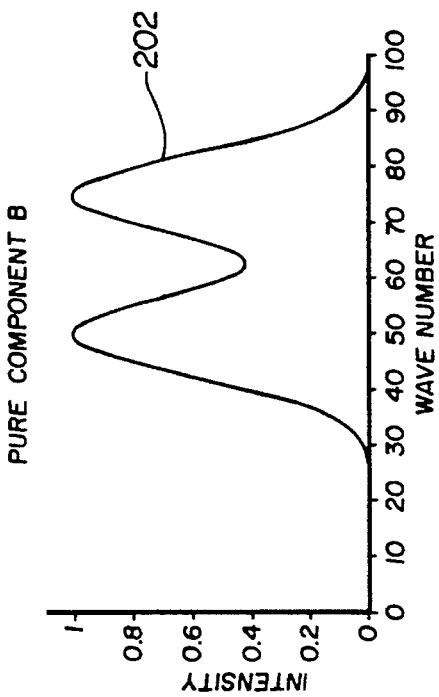
FIGS. 12 and 13 are graphs including spectra of two different pure components.
Figure 13:
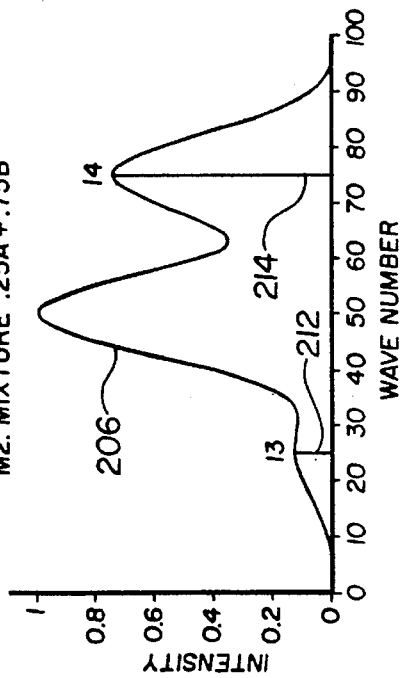
Figure 14:
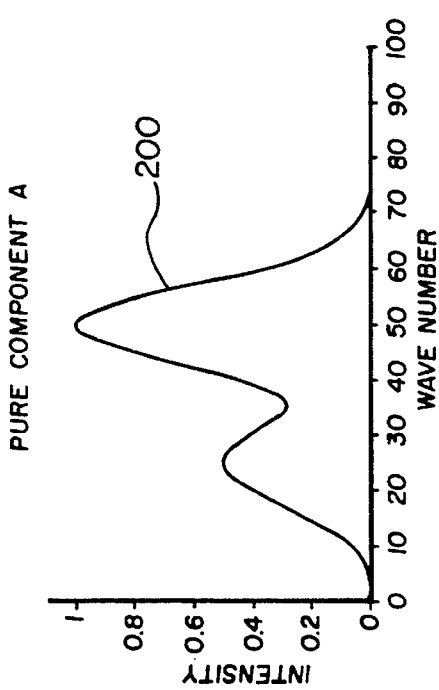
FIGS. 14 and 15 are graphs including spectra of two different mixtures each including the pure components of FIGS. 12 and 13.
Figure 15:
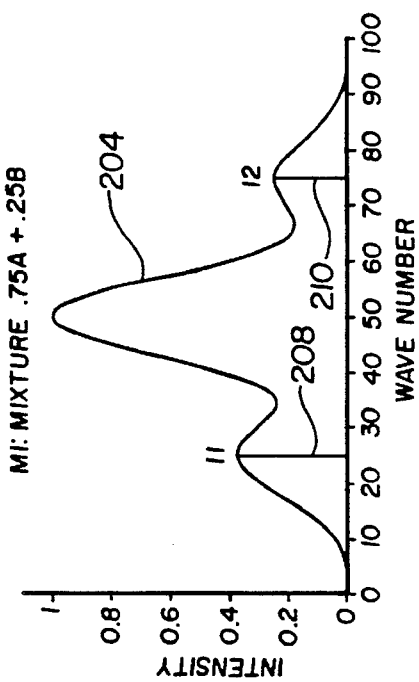

The present invention is further illustrated by the following description in conjunction with FIGS. 12–20. In FIG. 12, curve 200 is the spectrum of pure component A and in FIG. 13 curve 202 is the spectrum of pure component B. Curve 204 in FIG. 14 is the spectrum of a mixture M1 containing 75% pure component A and 25% pure component B. Curve 206 in FIG. 15 is the spectrum of a mixture M2 containing 25% pure component A and 75% pure component B. By comparing curve 204 with curves 200 and 202, it is apparent that the peak in curve 204 indicated by line 208 is a result of pure component A and that the peak indicated by line 210 is a result of pure component B. The intensities at the peaks are designated I1 and I2 in FIG. 14. Similarly, by comparing curve 206 with curves 200 and 202, it is apparent that the peak in curve 206 indicated by line 212 is a result of pure component A and that the peak indicated by line 214 is a result of pure component B. The intensities at the peaks are designated I3 and I4 in FIG. 15.

The mixtures shown in FIGS. 14 and 15 can be represented mathematically as follows:

I1(A)+I2(B)= M1
I3(A)+I4(B)= M2 where I1, I2, I3, I4,M1 and M2 are known and A and B are unknown. Therefore this system of two equations and two unknowns can be solved.

Figure 16:
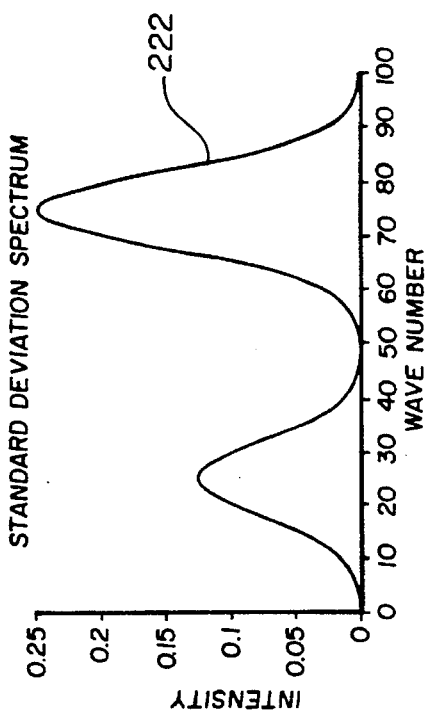
FIG. 16 is a graph including a mean spectrum of the mixtures of FIGS. 14 and 15.
Figure 17:
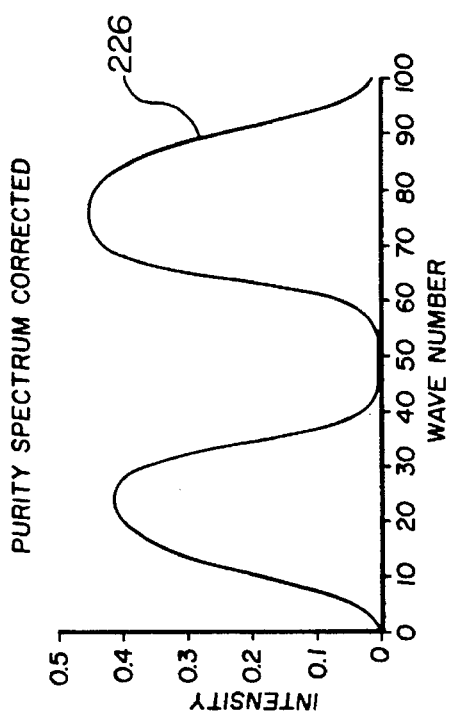
FIG. 17 is a graph including a standard deviation spectrum obtained from the spectra of FIGS. 14–16.
Figure 18:
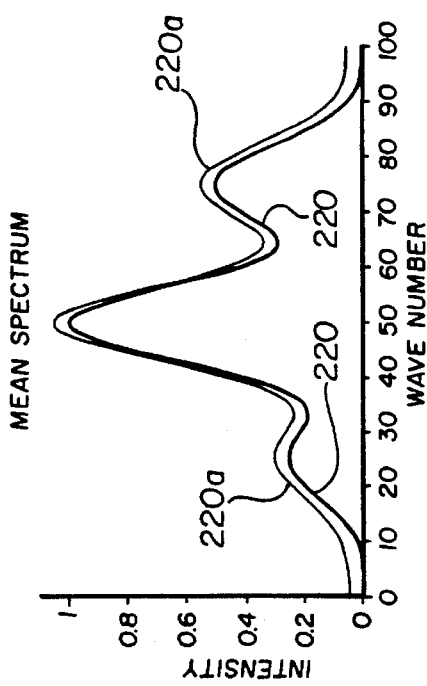
FIG. 18 is a graph including a purity spectrum obtained from the spectra of FIGS. 16 and 17.
Figure 19:
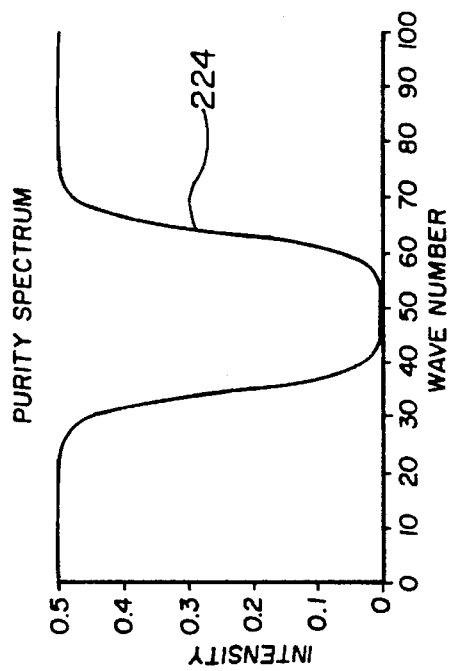
FIG. 19 is a graph including the noise corrected spectrum of FIG. 18.

In FIG. 16, curve 220 is the mean spectrum and is obtained by taking one half the intensity of mixture 1 and mixture 2 from FIGS. 14 and 15 at each wave number. For example, at wave number 20, the M1 intensity is about 0.3 from FIG. 14 and the M2 intensity is about 0.1 from FIG. 15. One-half the sum is 0.2 which corresponds to the value on curve 220 at wave number 20 in FIG. 16. In FIG. 17 curve 222 is the standard deviation spectrum obtained from the data in FIGS. 14, 15 and 16 using equation 4. Curve 224 in FIG. 18 is the purity spectrum and is obtained by dividing the standard deviation spectrum valve in FIG. 17 by the mean spectrum valve in FIG. 16 at each wave number. In FIG. 19, curve 226 is the purity spectrum corrected wherein the divisor includes the correction factor $\alpha$ previously described. The addition of $\alpha$ to the mean spectrum results in curve 220*a* in FIG. 16.

Figure 20:
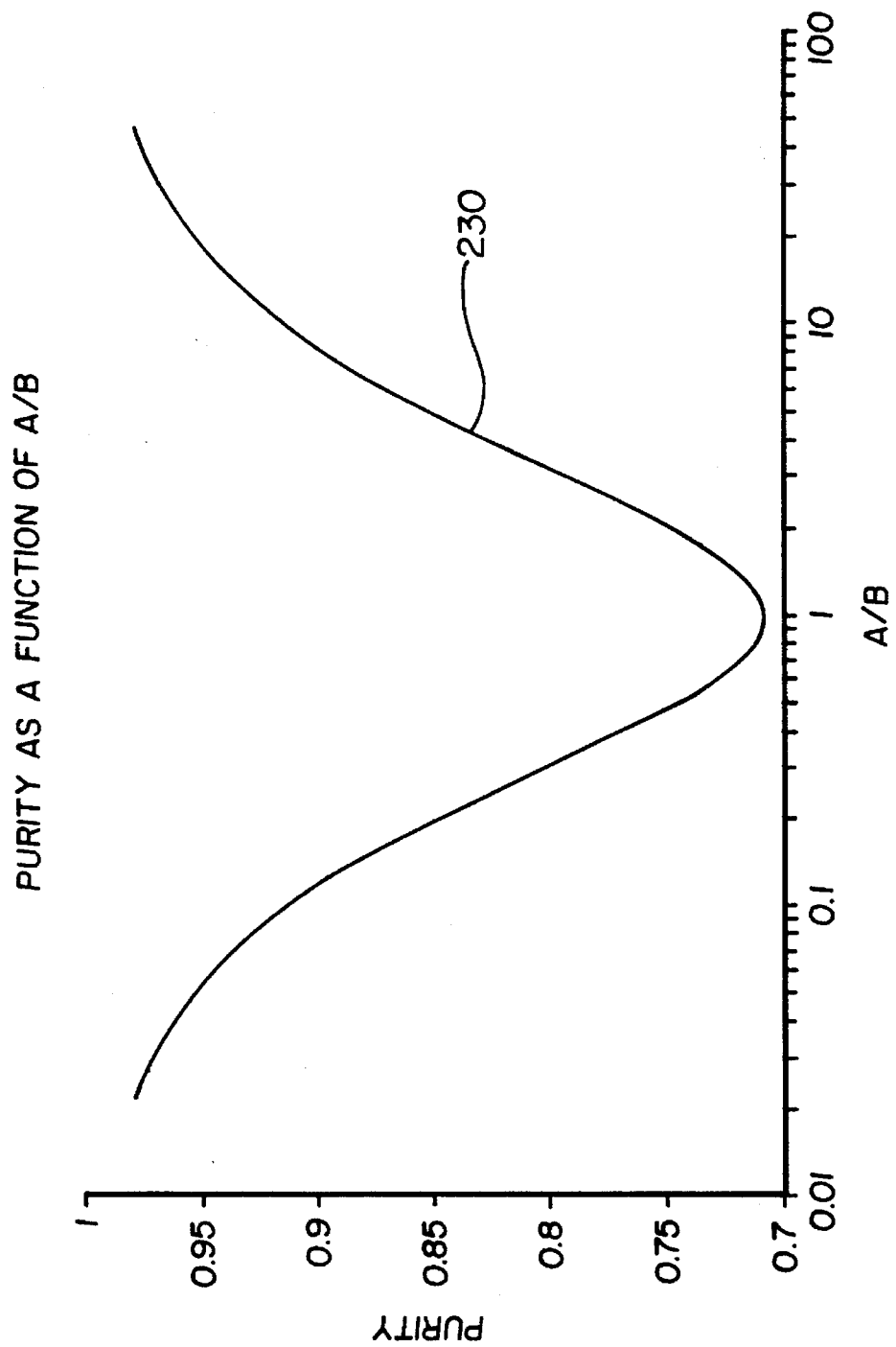
FIG. 20 is a graph including a purity spectrum as a function of a different variable.

FIG. 20 illustrates the principle behind the foregoing approach that the more independent sources of variance there are, the smaller the standard deviation becomes with respect to the mean: the principle of signal averaging. This is due to the fact that the combined means of the independent sources is the simple sum of the mean values, while the combined variance is the sum of the squares of the variance values of the independent sources. In mathematical terms this can be expressed in the following manner. Let component A have a mean of $\mu_1$ and standard deviation of $\sigma_1$ and component B have a mean of $\mu_2$ and standard deviation of $\sigma_2$. If a variable has a contribution a from component A and a contribution b from component B (the contributions are based, for example, on the absorptivity of a certain wave number for a certain component), the purity of that variable is as follows:

$$\text{purity} = \frac{\sqrt{a^2\sigma_1^2 + b^2\sigma_2^2}}{a\mu_1 + b\mu_2}$$

Using ratios the equation can be simplified to:

$$\text{purity} = \frac{\sqrt{r^2\sigma_r + 1}}{r\mu_r + 1}$$

where r=a/b, $\sigma_r=\sigma_1/\sigma_2$, $\mu_r=\mu_1/\mu_2$. This equation expresses purity as a function of r=a/b which is shown by curve 230 in FIG. 20, for $\mu_r=1$ and $\sigma_r=1$. For a/b $\approx 0$, i.e. only b, the purity is high, and for a/b$\approx\infty$, i.e. only a, the purity is high. In other words, the graph of this function in FIG. 20 shows that for increasingly high values of r (relatively high value of a) the value of this function increases, with a maximum value of one. For increasingly low values of r (relatively high value for b) the function also has increasingly high values, with a minimum in between. This shows that this function indeed expressed the purity of a variable properly. It is possible to prove with calculus that this is true for more complex cases, i.e. for mixtures of more than two components, and for cases where the variables are not independent, as is assumed in the first equation.

Another example illustrating the mode of operation of the present invention is an x-ray screen data set. A schematic of the cross section of the x-ray screen is provided in the upper portion of FIG. 21 which shows the regions of the components, i.e. PET (poly-ethylene terphthalate) 236, PVA (poly-vinyl acetate) 238 and PVA/PVC (co-polymer of 20% PVA and 80% poly-vinyl chloride) 240 based on a rectangular smoothing window, in order to emulate the effect of the size of the IR spot 242, which is also given. The data points are represented by *s 244 in FIG. 21. Note, that the IR spot is larger than several of the layers. The lower portion of FIG. 21 includes the expected profiles of PET, PVC and PVA designated 250,252 and 254, respectively. The reason why the profile of PVC is given rather than from PVA/PVC is that it is expected that the method of the present invention separates the PVA as a separate component, since it is also present in another layer. Since scanning the edges from the screen gives problems in the spectra and in order to give a relative high weight to the middle layer, only the range designated 244 in FIG. 21 was scanned. A sample of the obtained spectra is given in FIG. 22. For a lot of applications the standard deviation spectra suffice to resolve the spectra, as will be demonstrated by using this data set. Since noise may give problems, the noise level is set at 5% by applying equations 25–27 with and each having values of 0.05. The pure variable selection is indicated in FIG. 23. After selecting three pure variables, the diagnostic values indicate that the process may be finished, as indicated in Table V, although there are spectrum-like features in FIG. 23*d*.

TABLE V

Results with X-ray screen data.
Values of functions to determine rank

| $R_r$ | $R_p$ | $R_s$ | $R_t$ |
|---|---|---|---|
| 100.0000 | 100.0000 | 100.0000 | 4.8269 |
| 7.6082 | 17.8011 | 20.7172 | 36.8885 |
| 0.5391 | 1.007 | 0.5616 | 77.6195 |
| 0.0093 | 0.0152 | 0.0072 | |

The pure variable indicated in the fourth standard deviation spectrum appears to be in a range of the spectrum that does not contain any information. Furthermore, resolving the mixtures using this fourth pure variable results in spectra with a significant amount of negative intensities. This knowledge is a strong indication that the rank of the data is three. The spectra of the pure components and the associated concentrations are given in FIGS. 24 and 25, respectively.

Figure 24A:
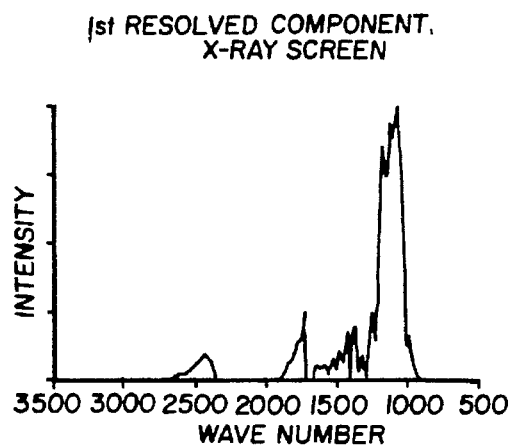
FIGS. 24a–24g are graphs including spectra obtained from the pure variable information of FIG. 23 wherein FIGS. 24a, c and d are the resolved spectra, FIGS. 24b, a and f are the spectra of the mechanically separated layers.
Figure 24B:
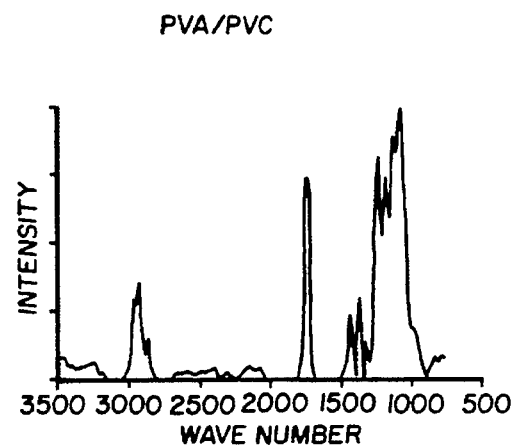
Figure 24C:
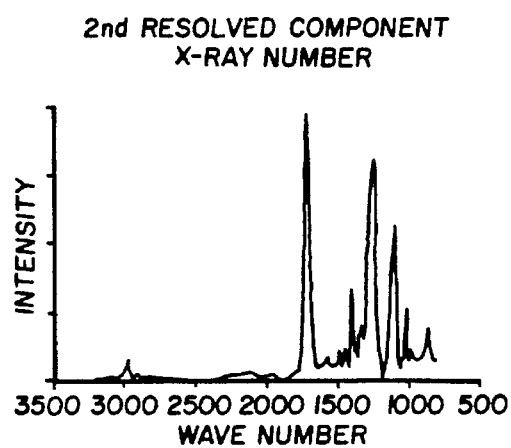
Figure 24D:
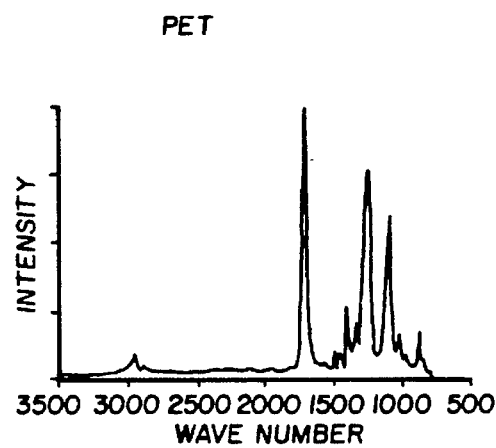
Figure 24E:
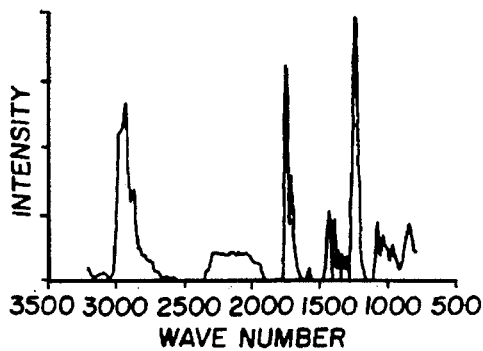
Figure 24F:
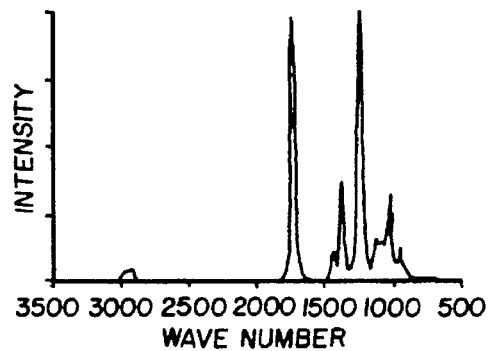
Figure 24G:
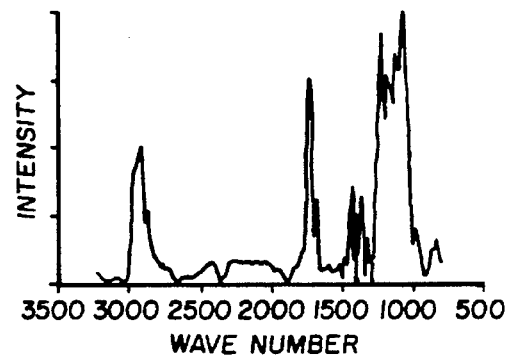

The first extracted spectrum in FIG. 24*a* has similarities with the model spectrum labeled PVA/PVC IN FIG. 24*b*. The spectrum in FIG. 24*b* is more complex of nature, because of the presence of the phosphor in the screen. Furthermore, since PVA is a separate component in the X-ray screen, it is expected that this first extracted spectrum represents PVA/PCV (+phos– phor) minus PVA. In order to demonstrate this, the other extracted components need to be discussed first. The second resolved component in FIG. 24*c* clearly resembles the model spectrum of PET in FIG. 24*d*. This is not so surprising, since PET is present in a pure form within the resolution of the IR spot in the screen. The last resolved component has similarities with PVA. There is a contribution of the methyl group around 2900 cm$^{-1}$, which is higher than expected, although PVA is the only source of the methyl group. Possible explanations are interactions, due to the phosphor, and/or the fact that PVA/PVC is not really a mixture of PVA and PVC, but a co-polymer. With this extracted PVA spectrum available, it is not possible to test the hypothesis that the first resolved component 'lacks' PVA. The sum of the 'PVC' spectrum and the PVA spectrum results in FIG. 24*g*, which is almost identical to the model spectrum of PVA/PVC in FIG. 24*b*. These results show that self-modeling mixture analysis can give a very reasonable estimate of the components in a polymer laminate.

Figure 21:
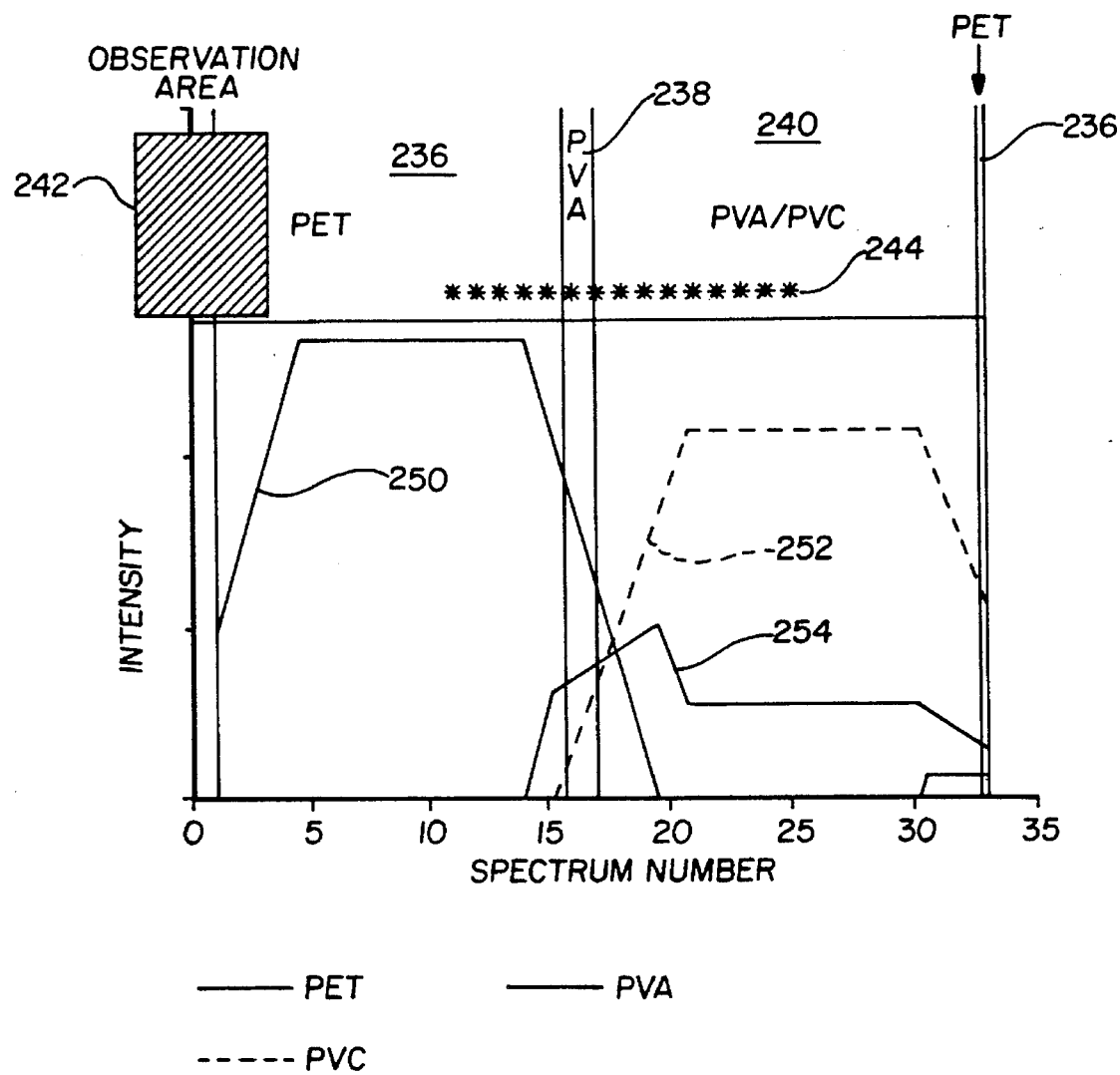
FIG. 21 is a combined schematic representation of the cross-section of an X-ray screen together with a graph of the concentration profiles of the components.
Figure 22:
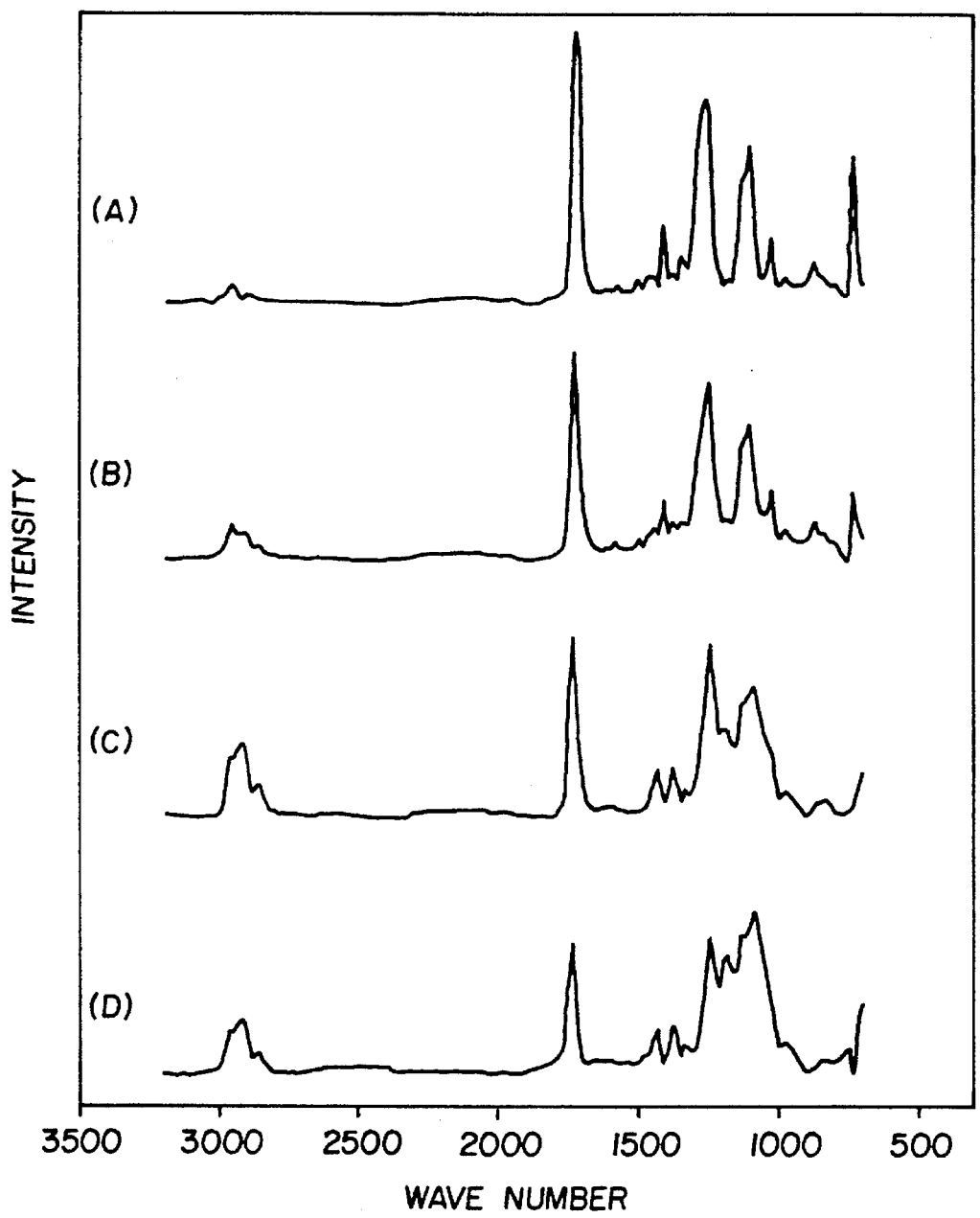
FIG. 22 is a graph including a sample of the obtained spectra of the X-ray screen represented in FIG. 21.
Figure 23A:
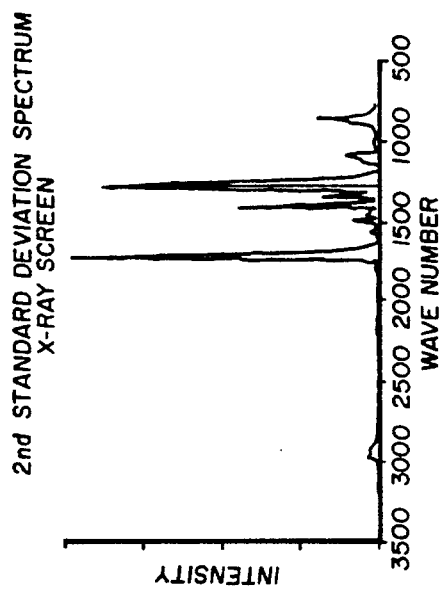
FIGS. 23a–23d are graphs including standard deviation spectra of the X-ray screen data of FIGS. 21 and 22 wherein the pure variables are indicated by vertical lines within the spectra.
Figure 23C:
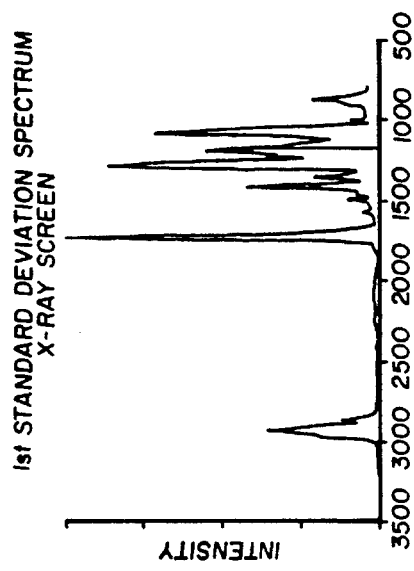
Figure 23B:
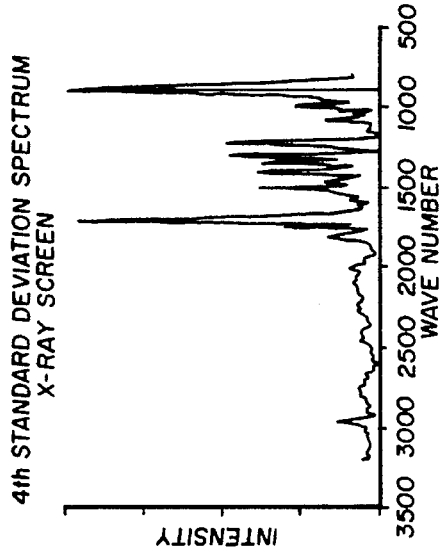
Figure 23D:
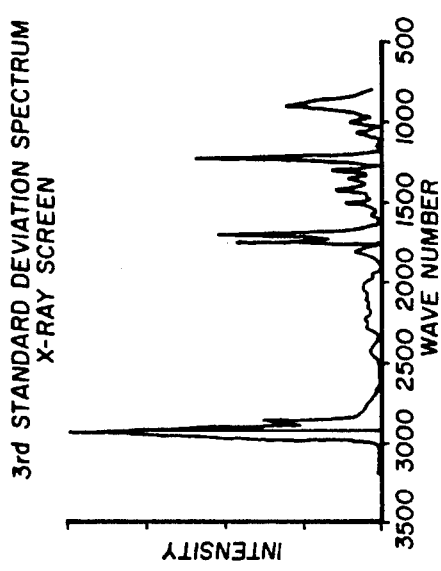
Figure 25:
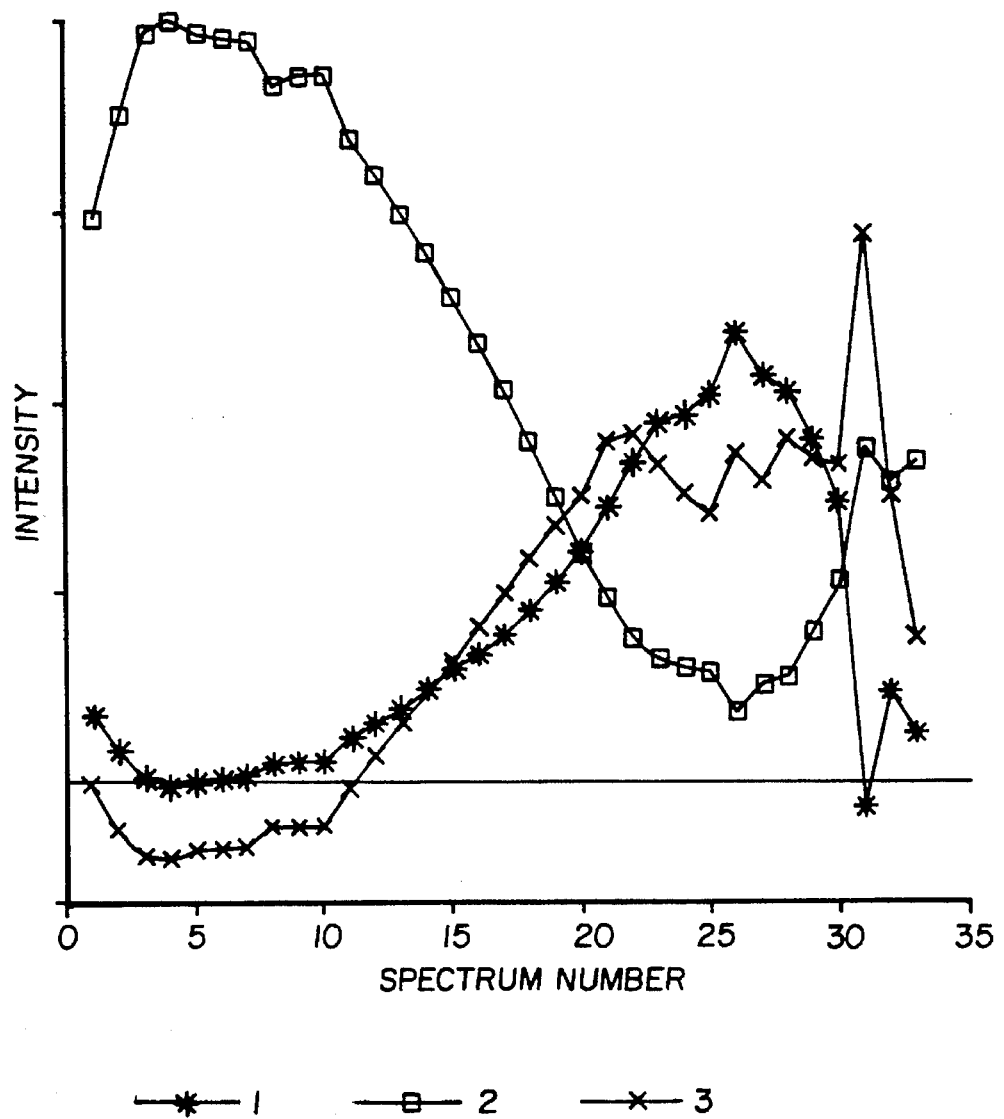
FIG. 25 is a graph including concentration profiles determined by the method of the present invention.

The concentration profiles of the extracted components in FIG. 25 include all the spectra. As mentioned above, only part of the spectra was used for the data analysis. It is possible, however, to calculate the least squares contribution of all the spectra by the proper use of equation 24. Since the edges of the laminate give problems in the spectra, the first few and the last few spectra have to be viewed with caution. It is obvious, though, that the curves closely match the expected profiles as given in FIG. 21. The estimated profiles in FIG. 21 are based on the assumption that equal weights of polymers results in equal spectral responses which is not very likely the case. This is the likely explanation why there are differences between the magnitude of the profiles in FIG. 21 and FIG. 25. The maximum around spectrum number 20 is due to the middle PVA layer, the thickness of which is below the resolution of the observation area. It is interesting to note that the PVA profile has a somewhat unexpected behavior in the PVA/PVC layer. The probable cause of this is the presence of the phosphor particles. The negative intensities in the PVA profile is very likely due to negative intensities in the original data set. This is caused by a less than optimal base-line correction procedure.

To summarize, the key equation employed in the mode of operation of the present invention is the one which calculates the jth pure(st) variable. The way the pure variable is identified is by its row index in the matrix D which, as previously described, has size v*c where v is the number of variables (e.g. wavenumbers, m/z values, etc.) and c is the number of cases (spectra, responses, etc.) For example, if the first pure variable is the sixth variable in the data set, the first pure variable P1 will have the value 6. The second pure variable will be identified as P2 etc. In equations, the kth pure variable (Pk) is defined as follows:

$$Pk=i \text{ for } MAX_i \, P_{i,j}$$

In words, the first pure variable is defined as the variable index i for which $P_{i,j}$ has its maximum, where $$P_{i,j}=w_{i,j}*\sigma_i/(\mu_1+\alpha)$$

where (for j=1)

$w_{i,1} \, (\lambda_i/\,(\lambda_i+\beta))^2$ and for j>1, the following determinants are calculated $$w_{i,j} = \begin{vmatrix} c_{i,i} & c_{i,P1} & \cdots & c_{i,P(j-1)} \\ c_{P1,i} & c_{P1,P1} & \cdots & c_{P1,P(j-1)} \\ \vdots & & \cdots & \vdots \\ c_{P(j-1),i} & \cdot & \cdots & c_{P(j-1),P(j-1)} \end{vmatrix}$$

where $C=(1/c) \, D \, (\lambda,\beta)D(\lambda,\beta)^T$
and where $D(\lambda,\beta)=d_{i,j}/(\lambda_i+\beta)$.

The values for $\alpha$ and $\beta$ are related to the mean and length. A typical value for $\alpha$ is 5% of the maximum value of $\mu_1$. For $\beta$ the typical value is 5% of the maximum value of $\lambda_i$. These values can be defined by the user.

Figure 26:
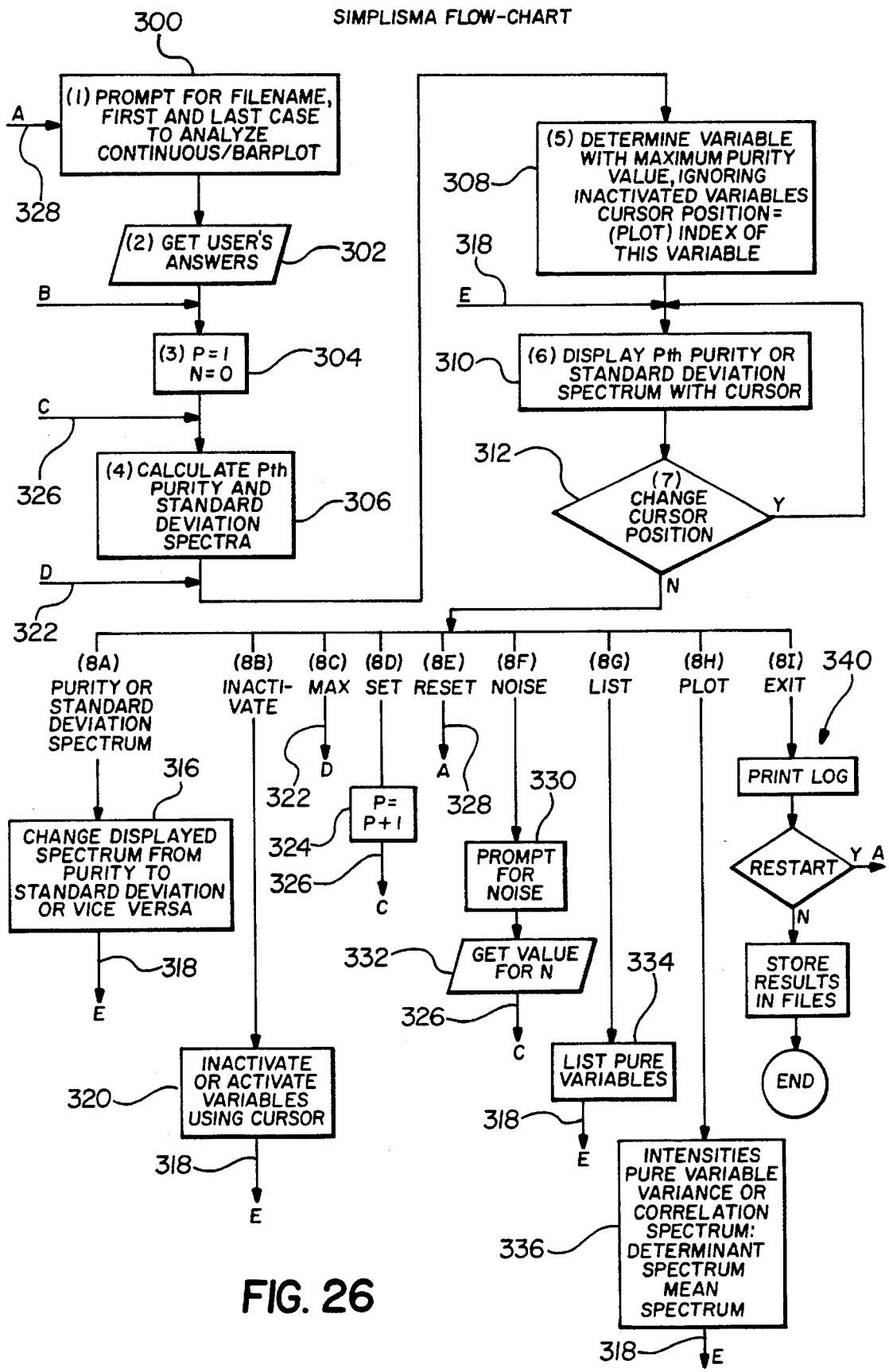
FIG. 26 is a schematic diagram including a flow chart of the portion of a computer program for determining the pure variables according to the method of the present invention.
Figure 27A:
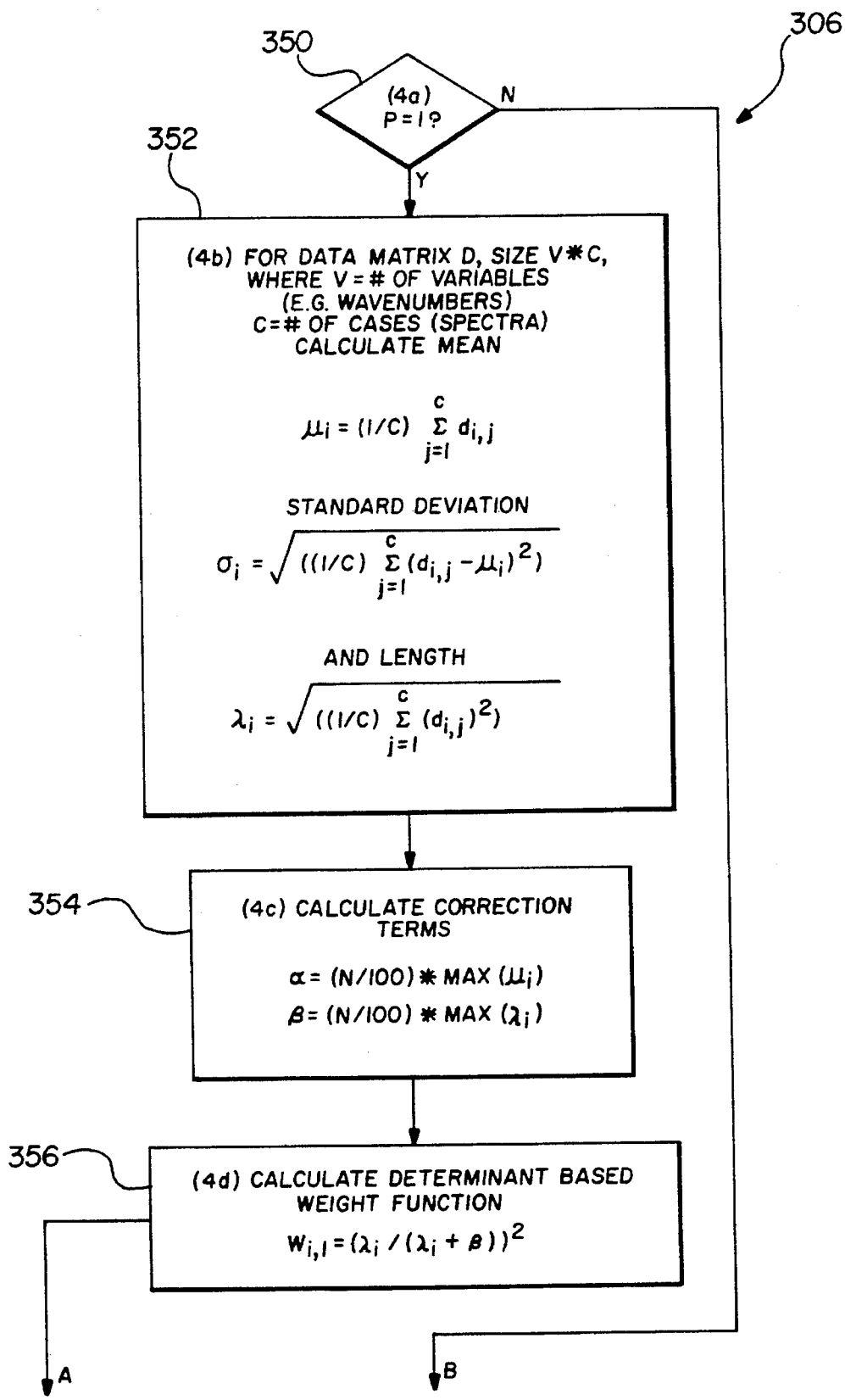
FIGS. 27a and 27b are schematic diagrams including flow charts detailing a portion of the program of FIG. 26;.
Figure 27B:
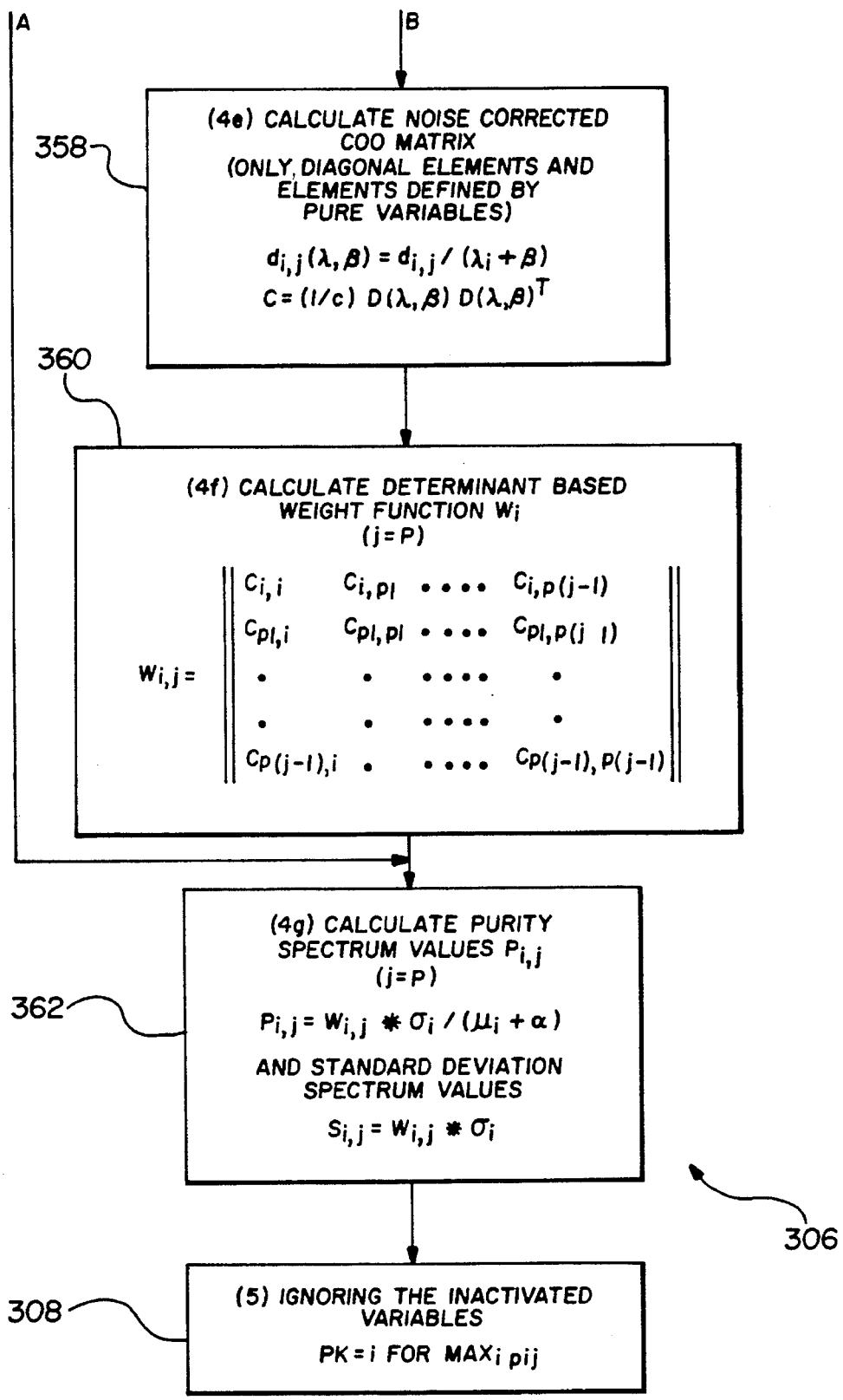
Figure 28:
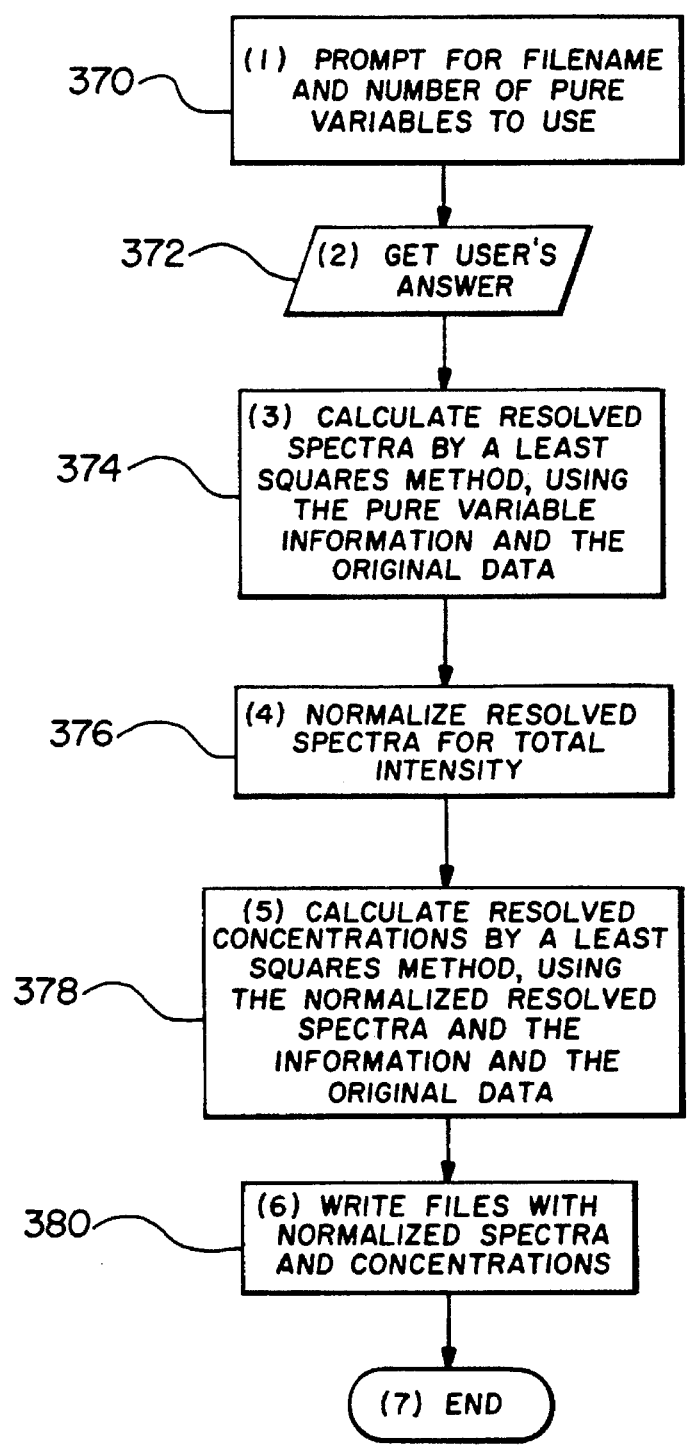
FIG. 28 is a schematic diagram including a flow chart of the portion of a computer program for resolving mixture data using pure variable information according to the method of the present invention.

A computer program for carrying out the mode of operation of the present invention is illustrated by the program flow charts of FIGS. 26–28. FIG. 26 shows the portion of the program for determining the pure variables, FIGS. 27*a* and 27*b* detail a portion of the program of FIG. 26, and FIG. 28 shows the portion of the program for resolving the mixture data using the pure variable information. Referring first to FIG. 26, block 300 asks for the name of the file in which the data to be analyzed are stored. The default filename is the previously used filename, i.e. after using the restart option described below. It is possible to analyze only part of the file by defining the first and last spectrum to analyze. The default for the first and last spectrum are the first and last spectrum in the spectrum or, after using the restart option, the same ones used before increased by one. This is done in order to facilitate analyzing the data using a moving window, which emulates an on-line type of application. Since spectral data are displayed in either bar graphs, e.g. mass-spectra, or continuous graphs, e.g. IR spectra, a choice needs to be made between these two options. Block 302 speaks for itself and requires no explanation.

In block 304 the variable P gets the value 1 during the process of determining the first pure variable, the value 2 during the process of determining the second pure variable, etc. The variable N stands for noise. The values for $\alpha$ and $\beta$ are calculated on the basis of this number. The value for N is the percentage of the maximum value of the mean taken for a and for the percentage of the maximum value of the length taken for $\beta$. At this point, the same percentage is used for both noise correction terms. Instead of basing the noise correction terms on maxima, other values are contemplated, such as the mean of the mean values, etc.

Using the means, standard deviations, lengths, the values for $\alpha$ and $\beta$ based on N and (P-1) pure variables defined by the SET option, the Pth purity and standard deviation spectra are calculated in block 306.

Block 308 determines the variable with the maximum purity value. The variable with the maximum value is the Pth pure (st) value. Variables that have been inactivated are ignored for the determination of the maximum value as will be explained. The basis for the determination in block 308 is the equation $$PK=i \text{ for } MAX_i P_{i,j}$$

described hereinabove.

In block 310 the pth purity or standard deviation spectrum is displayed. The program starts with the purity spectrum. After using the display 316 described herein option 316 this can be changed to a standard deviation spectrum, in order to facilitate comparison with the original spectra. The pure(st) variable is always based on the purity spectrum, even if the standard deviation spectrum is displayed. Colors are used to indicate the difference between the two spectra: green can be used for the purity spectrum and blue for the standard deviation spectrum. The so-called inactivated variables, which are ignored for the determination of the maximum purity value, can be colored red in the displayed spectrum. Next to the displayed spectrum, text also indicates whether it is a purity or a standard deviation spectrum and gives directions how to move the cursor. Furthermore, numerical values that assist the process of determining the number of component in the mixture are also displayed. The cursor is displayed at the position described as cursor position. This may either be at the variable with the maximum purity value or at a user defined position.

Block 312 indicates that the cursor position can be changed interactively. The set option described hereinafter uses the variables at which the cursor is present for its calculations. This is done since the variable with the maximum purity value may not be of interest to the research, e.g. if the selected pure variable is of a noisy character, if the selected pure variable represents a chemical component of no interest, or if (minor) adjustments need to be made in order to obtain a pure variable at the top of a peak. Other possibilities are to check the validity of the variables thought to be pure, e.g. according to literature or previous experiments or based on chemical knowledge.

After the cursor is defined by either the maximum purity value or the user, the following options are available to the user, displayed together with the purity or standard deviation spectrum. Using the option of block 316 results in changing the displayed Pth purity spectrum into the Pth standard deviation spectrum, or, if the standard deviation spectrum is displayed, it will be changed into the Pth purity spectrum. The routine returns through path 318 to block 310. In the option of block 320, variables can be inactivated for the determination of the maximum purity value by using the cursor. As mentioned above, inactivated variables are displayed with the color red in the bar or continuous spectral plot. The routine returns through path 318 to block 310. The option represented by path 322 puts the cursor at the variable with the highest purity value.

Block 324 sets the variables as defined by the cursor, which means that it will be treated as a pure variable for the calculation of the purity and standard deviation spectra. It will be obvious that P needs to be increased by a value of one. The routine returns through path 326 to block 306. The reset option 328 resets all the pure variables, i.e. for the next calculation of purity and standard deviation spectra no pure variables are used, resulting in the 1st purity and standard deviation spectrum. For these calculations, the noise is reset to 0. This is useful if one decides that another noise level needs to be used, or if one wants to see the effect of different pure variable selections.

The value for N can be changed in option 330, 332 which is the basis for the calculations of error correction terms in the purity and standard deviation spectra. The routine returns through path 326 to block 306, option 334 gives the possibility to list the pure variables selected until now. The routine returns through path 318 to block 310.

Several important plots can be made under option 336. The plot of the intensities of the variable defined by the cursor position in all the spectra is an important diagnostic tool in order to see if a variable is noisy or if a certain expected trend is present. The variance spectrum and the correlation spectrum show the relation of the variables defined by the cursor position with all the other variables. The variance spectrum shows the co-variances of the selected variable with all the other variables, which may give a first impression of the component described by that pure variable. The correlation does the same, but gives all the variables an equal weight. The determinant values of all the variables with respect to the pure variables selected plays an important part in the calculations, which is the reason why these values can be inspected in a spectral plot of these values. The determinant based approach to determine pure variables is done here by moving the cursor to the variable with the maximum value in the determinant spectrum. Next to the standard deviation spectrum (i.e. the 1st standard deviation spectrum with noise level 0), the mean spectrum is also a valuable tool to evaluate the data, which is the reason why it is one of the display options. The routine returns through path 18 to block 310.

The exit option 340 is used after all the pure variables have been determined. This is generally clear from the purity and standard deviation spectra in combination with the numerical values calculated for this purpose. In some cases it is not obvious how many components there are. The program to calculate the pure variables has the option to limit the number of pure variables used in the calculations, in other words, it never harms to select a few 'extra' pure variables. After using the exit option, a log of the process is displayed on the screen or printer, which contains information such as the filename used, the range analyzed, the numerical values to determine the number of components in the data set, the pure variables selected and the names of files which will be written on a disk. Some of these files are needed for the program that resolves the spectra. The files can also be used for plotting purposed or as input for other types of data analysis programs. If no restart is required, all the data will be written in files, as mentioned above. This restart option is mainly useful to emulate an on-line type of application and also useful for other research purposes where only the log is required.

FIGS. 27a and 27b show in further detail the routine represented by the block 306 in FIG. 26. Block 350 indicates that the actions for the first pure variable are different from the other ones. Block 352 illustrates the basic statistics needed for the calculations. With respect to block 354 the noise correction term β needs to be relatively small with respect to all the mean values and the noise correction term B needs to be relatively small with respect to all the length values. At this point these values are selected with respect to the maxima of the mean and the length values, respectively. Other criteria are, for example with respect to the mean of the mean values and the mean of the length values, respectively.

Block 356 represents the diagonal values of the noise corrected COO(coorelation around the origin) matrix, which are the maximum values of the determinant based weight function. Block 358 describes calculation of the noise corrected COO matrix. From the determinant given in block 360 it will be clear that not all the values of the noise corrected COO matrix are needed. For versions of the program where speed and memory play a crucial role, the limitation of the calculations for the COO matrix may be important. Furthermore, for the successive calculation of the determinant based weight function, most of the elements will stay the same, which can also be used to build an efficient algorithm by updating the noise corrected COO matrix rather than recalculating it. The determinant as given in block 360 is symmetrical. Fast algorithms can be used to utilize this property. The calculation of the values used for the purity spectrum ($p_{i,j}$) and the standard deviation spectrum ($s_{i,j}$) is shown in block 362.

With respect to block 308 in FIG. 26, the index of the variables with the highest purity value needs to be known, since this defines the pure(st) variable. Another option of the program, not indicated in the flow diagram, is to base the index on the maximum value of the determinant based weight function. Inactivated variables are variables that need to be ignored for the search of the maximum. The inactivated variables are visible in the plot of the spectra by a color marking.

FIG. 28 illustrates the portion of the program for resolving the mixture data, using the pure variable information. In blocks 370 and 372 the user needs to give the name of the file with the original data. The program automatically reads in the file with the pure variable information. The option of giving the number of pure variables to use is a very useful one. It is not always clear how many useful components there are in a data set. For example, a fourth pure variable may be based on interactions between components rather than changes in the concentrations of a chemical component. Including this variable may result in resolved spectra with negative intensities, which is an indication that only three pure variables need to be used.

Block 374 illustrates resolving the data into the spectra of the pure components which is a standard least squares calculation, widely used in chemometrics. With respect to block 376 the intensities of the variables in the resolved spectra depend on the intensities of the pure variables used. Assuming that equal amounts of the components result in equal responses in the spectrometer, the spectra are normalized in such a way, that the total intensities of the resolved spectra are all the same, before these spectra re used to calculate the concentrations.

Although the intensities of the pure variables basically reflect the concentrations of the components (after correcting for the normalization procedure described above), it was decided to calculate a least squares approximation of the concentrations, since this describes the data set better. This calculation in block 378 results in a noise reduction similar to principal component analysis.

In block 380 the spectra are stored and can be plotted with other available programs. Next to the resolved spectra and concentrations, several related files are written, i.e. with the spectral intensities divided by the lengths of the variables, which gives the relative contribution of the variables. Another useful format is the spectra minus the mean of the data set, which enhances the typical properties of the components. This is especially useful if the mixtures contain more spectra than can possibly be resolved.

The program shown in FIGS. 26-28 can be un on a COMPAQ 386/20 computer, with a memory extension to 640 K (A DOS limit). A math co-processor is used. The program is written in FORTRAN 77. As a consequence, the program can be run on an IBM-PC compatible computer. Commercially available graphic subroutines are used for the graphics. An example of such software is commercially available from Media Cybernetics, Silver Spring, Md. under the designation Halo '88. Due to relatively simple approach, versions can be developed that can run on smaller computer.

For data that are categorized, i.e. the spectra belonging to a certain number of categories (e.g. a set of spectra of batch A, a set of spectra of batch B, etc.) the following procedure can be used. Instead of the standard deviation, the ratio of the standard deviation between the groups and the standard deviation with the groups can be taken. Instead of the mean of the whole data set (grand mean), the mean of the category means is used. Instead of calculating the resolved spectra on the basis of the intensities of the pure variables, the spectra can be calculated on the basis of the category means, i.e. each intensity is replaced by its category mean value. This results in a discriminant analysis type of approach.

In some cases, the expected concentration profiles are thought to be known. Assume that three concentration profiles are known. These profiles can be added to the data set as variables, i.e. as rows to the data set D. The user selects these three variables as the pure ones (by using the cursor). If the concentration profiles are correct estimated of the concentration as present in the original data set, the fourth purity/standard deviation spectrum will represent only noise. If not, the fourth purity spectrum will show a pattern. The resolved spectra will also aid this process.

The present invention can be used to test pure variables known by other means, e.g. chemical knowledge or theoretical considerations. This interaction possibility enables this approach to be like that of an expert system. In addition, the mode of operation of the present invention could be combined with an expert system to analyze spectra.

The approach provided by the present invention assumes the presence of pure variables. If the variables are not pure, the results may still yield valuable information, though the concentrations will have an offset, and the extracted spectra will show the typical features of that component in an enhanced way. There are approaches, however, that make it possible to deal correctly with pure variables. These approaches can be adapted for the approach of the present invention. These methods are designed for time-resikved data. The pure variables of such a data et show an overlap. The maximum of a curve is determined. This maximum is used in a delta function as a first approximation for the curve. A least squares approximation of this curve with the data set (similar to the way the concentrations are calculated in the method described herein) is calculated. The curve generally will have undesired properties, such as negative intensities. These negative intensities are made into 0, and the newly obtained curve is used to calculate a least squared approximation. This process is continued until the curve does not longer change significantly.

In case no pure variables are present, an iterative procedure can be applied in order to resolve the system, similar to procedures applied to principal component analysis based algorithms. In order to optimize the application to categorized data, a weight function that optimizes the discrimination of the categories can be used to calculate the purity and standard deviation spectra. In order to resolve the data, the intensities of the pure variables in the original data are replaced by their category means. As an alternative to calculating the purity of variables, the purity of the spectra can be calculated by the method of the present invention simply by transposing the data matrix. In addition, the mode of operation of the present invention can be applied to other forms of data besides spectra, such as data curves from compositional mixtures, for example X-ray provides diffraction patterns and chromatograms, and such as other data which exhibit a response to chemical or Physical properties.

Figure 29:
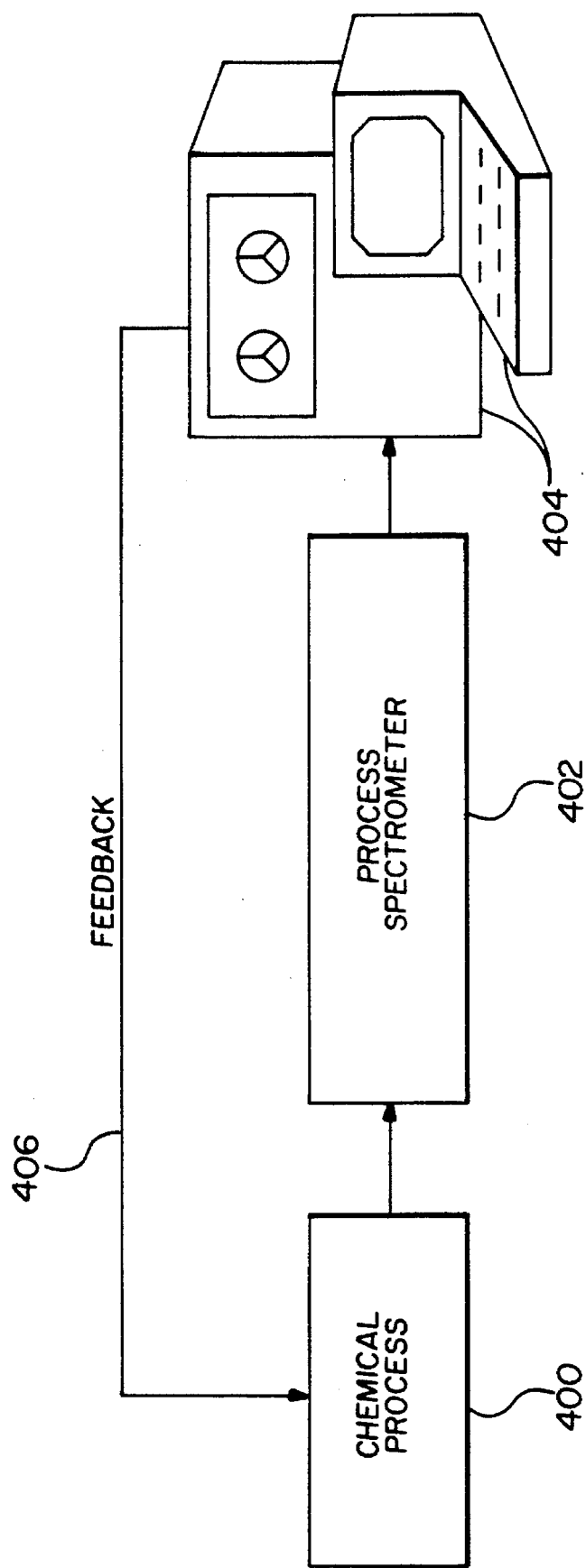
FIG. 29 is a schematic diagram of a process monitoring/control arrangement utilizing the method of the present invention.
Figure 30:
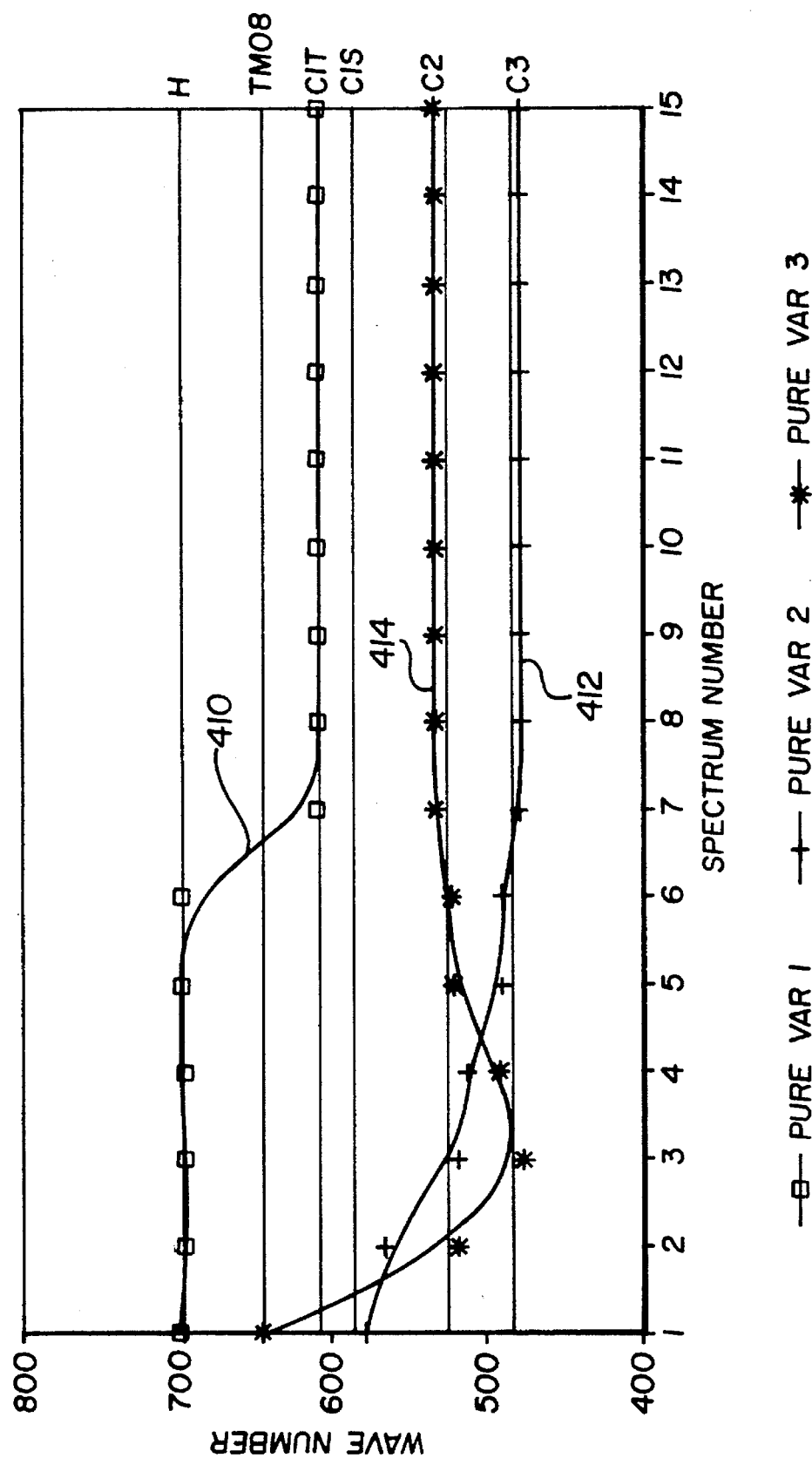
FIG. 30 is a graph including a pure variables plot obtained from the arrangement of FIG. 31.
Figure 31:
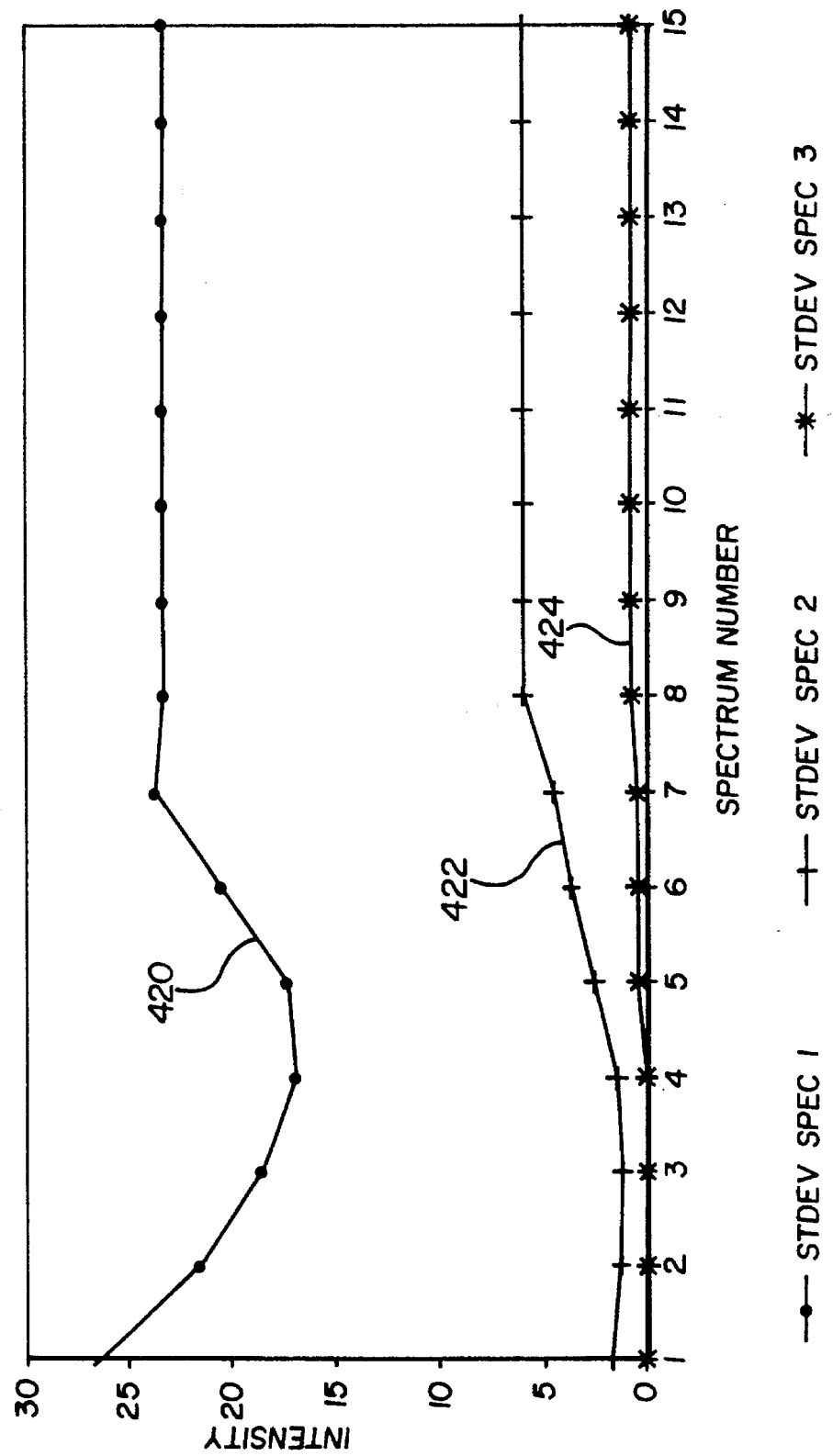
FIG. 31 is a graph including purity/standard deviation spectra determined by the pure variables of FIG. 30.

FIGS. 29–31 illustrate the manner in which the invention can be used for process monitoring/process control. FIG. 29 shows a setup for process control including a process 40,, process spectrometer 402, apparatus in the form of a computer 404 for analyzing data from spectrometer 402 and a feedback loop 406. If there is no feedback between the data analysis results and the chemical process, it is process monitoring. The data used follow a reaction in time. By way of example, the starting material is TMOS (tetramethyl orthosilicate), which, under the proper circumstances forms hydrolysis and condensation products. Referring to FIG. 30, the hydrolysis products are indicated by H, the condensation products by C1, C2 and C3, respectively. The method is to follow the pure variables of the data set as a function of time. This is emulated by first analyzing spectrum 1–9. The three pure variables obtained were plotted at the first point on the x-axis. Next, the spectra 2–10 of the data were analyzed, and the three pure variables were plotted at point 2. etc. A curve 410 determined by these points 'connects' the points. The first pure variable represents the hydrolysis product (H) (the literature value of 696 cm$^{-1}$ for this product as indicated by a line in FIG. 30) during the first 6 runs (a run is the analysis of a set of 9 spectra), which is indeed the major product during the first part of the reaction. Next, the first pure variable describes the first condensation product C1, which is also within expectations, since this is a major product after the hydrolysis reaction.

The second pure variable starts in the region for the first condensation product C1 (the first condensation product has a peak at 608 cm$^{-1}$ and a shoulder at 586 cm$^{-1}$) and then changes to the second (C2) and third (C3) condensation product, which again is to be expected. Curve 412 is determined by these points. The third pure variable describes TMOS for the first run, which is within expectations. Next it describes the condensation products. Curve 414 is determined by these points. Note that C2 and C3 are alternatively described by the second and third pure variables, which describes the relative importance of the changes of these components in the data set. What may look confusing is the lack of C1 between the data points 2 and 6. This is not so surprising, after all, since C1 first increases, and later in the reaction decreases, with a maximum relatively stable region in between. This stable region explains the lack of a pure variable due to this C1 product: the pure variable approach only picks up changes (the standard deviation is 0 if no changes occur). One has to realize that pure variables in the literature are not necessarily the same as determined by the approach of the method of the present invention.

It appears that this pure variables plot is a proper representation of the reaction. Deviations in the reaction will result in other pure variables and/or other order of the pure variables. These deviations can be picked up by algorithms, by using the know pure variables and their patterns in time as a reference. Furthermore, once a deviation has been detected, the resolved .spectra and their concentrations can be calculated, which is a powerful tool for trouble-shooting. The use of the information to correct a process may be suited for process control purposes.

Next to the pure variables, the total intensities (or related measure) of the purity or standard deviation spectra can be plotted as shown in FIG. 31. The first, second and third pure variables determine the curves 420, 422 and 424, respectively. This plot shows that the third pure variable need to be used with caution, since the intensity is so low for the first 4–5 runs. It appeared, however, that the third pure variable shows a pattern in FIG. 30, properly describing the reaction. This pattern can also be used (also in combination with the data in FIG. 30) to monitor a reaction. A fourth pure variable (not shown) basically has a zero intensity in this experiment. If the reaction deviated from the normal pattern, a fourth component may arise, which will be clear from an increase of the intensities used in this plot.

Thus, if one wants to monitor whether a certain product is a mixture of three known pure components, one can use pre-determined pure variables. Normally the fourth purity spectrum (and standard deviation) will have an intensity close to zero and show a noise pattern. In case another component (e.g. a contamination) is present, this will be clear from its presence in the fourth purity (and standard deviation) spectrum.

Another approach is the following. An automated version of the method assigns (for a three component system) three previously determined pure variables the fourth purity/standard deviation spectra should basically represent noise and have a negligible total intensity. If the process goes wrong, a possible fourth component will show up in the fourth purity/standard deviation spectrum, which may again be used for trouble-shooting and/or process control.

In other words, the pure variables are determined in an automated way. For a stead process, the pure variables will stay the same. Furthermore, a fourth pure variable will show an inconsistent behavior, due to the fact that only noise is left. If the process is changed, the pure variables will change and/or the fourth pure variable will show an inconsistent behavior (due to a fourth component).

Another variation to these approaches is to transpose the data matrix. Instead of the purity of the variables, the purity of the spectra will be calculated, which can be used in similar ways, as described above.

It is therefore apparent that the present invention accomplishes its intended objects. The results shown above and with several other data sets (not shown) always give very comparable results with the results of the principal component analysis approach. At this point, the mode of operation of the present invention did not fail to resolve data sets that were resolved before using the principal component analysis approach. It would appear that for very noisy data sets, principal component analysis will perform better. A clear advantage of the present invention is that it displays all the intermediate results in the form of spectra, which clearly facilitates a proper interaction with the operator. As was shown above, an improperly selected pure variable can be detected easily. If desired, the operator can move a cursor, to direct the pure variable selection. If an operator feels more comfortable with the maximum in the standard deviation spectrum it can just as well be selected, since the intensity of this wavenumber in the purity spectrum is very close to the maximum. Another possibility is to test the validity of the wavenumbers given as typical for the components: the extracted spectra will show the operator the effect of the selections. Another important point is that the successive steps make intuitive sense (e.g. the noise correction and 'eliminating' the effect of selected pure variables) which is not the case for principal component analysis. These results combined make the present invention promising for routings data analysis for which no highly skilled operator is needed in contrast with the principal component analysis based method.

While embodiments of the present invention have been described in detail, that is for the purpose of illustration, not limitation.

I claim:

1. Apparatus for controlling a process wherein starting material undergoes a reaction over a period of time to produce reaction products, said apparatus comprising:
    a) process spectrometer means operatively associated with said process for providing spectrographic data from said process;
    b) programmed computer means operatively connected to said process spectrometer means for analyzing said spectrographic data to determine pure variables relating to the reaction products and for comparing the determined pure variables to predetermined pure variables; and
    c) control means operatively associated with said process and operatively connected to said computer means for controlling the process in a manner determined by the result of the comparison.

2. Apparatus according to claim 1, wherein said computer means is programmed to analyze said spectographic data by performing the following steps:
    a) providing said spectrographic data of the material in the form of compound variables which have contributions from the components of the material;
    b) determining the purity values of said compound variables and presenting said purity values in the form of a first purity spectrum;
    c) finding the maximum of said purity values which is the first pure variable which has a contribution from only a first one of the components of said material;
    d) calculating a determinant-based weight function with respect to said first pure variable to eliminate the effect of said first pure variable;
    e) multiplying the first purity spectrum by said determinant-based weight function and presenting the results in the form of a second purity spectrum;
    f) finding the maximum of said purity values in said second purity spectrum which is the second pure variable which has a contribution from only a second one of the components of said material; and
    g) repeating steps d), e) and f) for successive determinant-based-weight functions with respect to preceding pure variables and presenting the results in the form of successive purity spectra for finding successive maxima to yield successive pure variables until the product of a determinant-based weight function and a purity spectrum does not have spectral features thereby indicating that no additional pure variables exist.

3. Apparatus according to claim 2, wherein said step of determining purity values comprises calculating the mean and the standard deviation of the magnitudes of said compound variables and calculating the ratio of the standard deviation to the mean for each of said compound variables.

4. Apparatus according to claim 3, further including a step of displaying the calculated standard deviation values in the form of a spectrum.

5. Apparatus according to claim 3, wherein a noise correction is applied to the purity calculation.

6. Apparatus according to claim 3, wherein a noise correction term is added to the denominator in the ratio of standard deviation to the mean calculated for each of said compound variables 7. Apparatus according to claim 6, further including a step of displaying the noise corrected purity values.

8. Apparatus according to claim 2, further including a step of displaying selected ones of said purity spectra.

9. Apparatus according to claim 2, wherein said step of determining purity values includes correcting for noise.

10. Apparatus according to claim 2, wherein said determinant-based weight function has a value of zero for the first pure variable and a high value for the other pure variables.

11. Apparatus according to claim 2, wherein said repeating steps d), e) and f) said successive determinant-based weight functions have zero values for preceding pure values and high values for remaining pure variables.

12. Apparatus according to claim 2, wherein a noise correction is applied to the calculation of the determinant-based weight function.

13. Apparatus according to claim 2, wherein said pure variables determined are used with said spectral data of the mixture for obtaining the components corresponding to the pure variables.

14. Apparatus according to claim 13, wherein said step of obtaining spectra of pure components is performed by a least squares method.

15. Apparatus according to claim 13, further including calculating the concentration of the components of said mixture using the spectra of the pure components with the spectral data of the mixture.

16. Apparatus according to claim 15, wherein said step of calculating the concentration of the components is performed using a least squares method.

17. Apparatus according to claim 1, wherein said computer means is programmed to analyze said spectrographic data by performing the following steps:
    a) providing said spectrographic data of the material in the form of compound variables which have contributions from the components of the material and which have intensities or magnitudes;
    b) placing said spectrographic data in a data matrix D having size v*c wherein v is the number of compound variables comprising the rows of the matrix and c is the number of spectra comprising the columns of the matrix and wherein the elements of the matrix are the intensities or magnitudes of the compound variables;

c) calculating for said data matrix D the mean $$\mu_1 = (1/c) \sum_{j=1}^{c} d_{i,j}, \text{ standard deviation}$$

$$\sigma_i = \sqrt{\left((1/c) \sum_{j=1}^{c} (d_{i,j} - \mu_i)^2\right)}$$

and compound variable length $$\sqrt{\lambda_i = \left((1/c) \sum_{j=1}^{c} (d_{i,j})^2\right)}$$

wherein d is each data value in said matrix D in row i column j;

d) calculating noise correction terms $\alpha = (N/100)*\text{Max}(\mu_i)$ and $\beta = (N/100)*\text{Max}(\lambda i)$ where N is a predetermined noise correction value;

e) calculating a first determinant-based weight function $W_{i,1} = (\lambda i/(\lambda i + \beta))^2$;

f) calculating purity spectrum values $p_{i,j} = w_{i,j} * \sigma_i/(\mu_i + \alpha)$ and standard deviation spectrum values $S_{i,j} = W_{i,j} * \sigma_i$ where j=P;

g) determining the variable with maximum purity value using $P_k = i$ for $\text{Max}_i P_{i,j}$ where k=1 which is the first pure variable;

h) displaying a selected one or both of the first purity spectrum and standard deviation spectrum;

i) calculating a correlation around the original matrix COO by first scaling the data matrix D by $d_{i,j}(\lambda,\beta) = d_{i,j}/(\lambda_i + \beta)$ and then calculating the matrix $C = (1/c) D(\lambda,\beta) D(\lambda,\beta)^T$ thereby giving all the compound variables an equal contribution in subsequent calculation of a determinant-based weight function;

j) calculating a second determinant-based weight function $$W_{i,j} = \begin{Vmatrix} C_{i,i} & C_{iP1} & \ldots & C_{iP(j-1)} \\ C_{P1,i} & C_{P1,P1} & \ldots & C_{P1,P(j-1)} \\ \cdot & \cdot & \ldots & \cdot \\ \cdot & \cdot & & \cdot \\ \cdot & \cdot & & \cdot \\ C_{P(j,i),i} & \cdot & \ldots & C_{P(j-1),P(j-1)} \end{Vmatrix}$$

where j=P;

k) calculating purity spectrum values $p_{i,j} = W_{i,j} * \sigma_i/(\mu_i + \alpha)l$ and standard deviation spectrum values $S_{i,j} = W_{i,j} * \sigma_i$ using said second determinant-based weight function;

l) determining the variables with maximum purity value using $P_k = i$ for $\text{Max}_i p_{i,j}$; and m) displaying selected ones or both of additional purity spectra and standard deviation spectra.

18. Apparatus according to claim 17 wherein said step of utilizing the pure variables comprises the steps of:

a) calculating resolved spectra by a least squares method using pure variable information and the spectral data of the mixture;

b) normalizing the resolved spectra for total intensity;

c) calculating resolved concentrations by a least squares method using the normalized resolved spectra, the pure variable information and the spectral data of the material; and d) displaying the normalized resolved spectra and the resolved concentrations.

* * * * *